US007914988B1

(12) United States Patent
Chudin et al.

(10) Patent No.: US 7,914,988 B1
(45) Date of Patent: Mar. 29, 2011

(54) GENE EXPRESSION PROFILES TO PREDICT RELAPSE OF PROSTATE CANCER

(75) Inventors: Eugene Chudin, Kirkland, WA (US); Jean Lozach, San Diego, CA (US); Jian-Bing Fan, San Diego, CA (US); Marina Bibikova, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 350 days.

(21) Appl. No.: 11/732,481

(22) Filed: Apr. 2, 2007

Related U.S. Application Data

(60) Provisional application No. 60/787,868, filed on Mar. 31, 2006.

(51) Int. Cl.
C12Q 1/68 (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 4,469,863 A | 9/1984 | Ts'o et al. |
| 5,034,506 A | 7/1991 | Summerton et al. |
| 5,216,141 A | 6/1993 | Benner |
| 5,235,033 A | 8/1993 | Summerton et al. |
| 5,324,633 A | 6/1994 | Fodor et al. |
| 5,386,023 A | 1/1995 | Sanghvi et al. |
| 5,429,807 A | 7/1995 | Matson et al. |
| 5,436,327 A | 7/1995 | Southern et al. |
| 5,451,683 A | 9/1995 | Barrett et al. |
| 5,482,867 A | 1/1996 | Barrett et al. |
| 5,491,074 A | 2/1996 | Aldwin et al. |
| 5,561,071 A | 10/1996 | Hollenberg et al. |
| 5,583,211 A | 12/1996 | Coassin et al. |
| 5,602,240 A | 2/1997 | De Mesmaeker et al. |
| 5,624,711 A | 4/1997 | Sundberg et al. |
| 5,637,684 A | 6/1997 | Cook et al. |
| 5,644,048 A | 7/1997 | Yau |
| 5,658,734 A | 8/1997 | Brock et al. |
| 5,744,305 A | 4/1998 | Fodor et al. |
| 5,795,716 A | 8/1998 | Chee |
| 5,831,070 A | 11/1998 | Pease et al. |
| 5,837,858 A | 11/1998 | Brennan |
| 5,856,101 A | 1/1999 | Hubbell et al. |
| 5,858,659 A | 1/1999 | Sapolsky et al. |
| 5,874,219 A | 2/1999 | Rava et al. |
| 5,919,523 A | 7/1999 | Sundberg et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,022,963 A | 2/2000 | McGall et al. |
| 6,025,601 A | 2/2000 | Trulson et al. |
| 6,033,860 A | 3/2000 | Lockhart et al. |
| 6,083,697 A | 7/2000 | Beecher et al. |
| 6,090,555 A | 7/2000 | Fiekowsky et al. |
| 6,136,269 A | 10/2000 | Winkler et al. |
| 6,200,756 B1 | 3/2001 | Herman et al. |
| 6,266,459 B1 | 7/2001 | Walt et al. |
| 6,287,768 B1 | 9/2001 | Chenchik et al. |
| 6,287,776 B1 | 9/2001 | Hefti |
| 6,288,220 B1 | 9/2001 | Kambara et al. |
| 6,291,183 B1 | 9/2001 | Pirrung et al. |
| 6,291,193 B1 | 9/2001 | Khodadoust |
| 6,297,006 B1 | 10/2001 | Drmanac et al. |
| 6,309,831 B1 | 10/2001 | Goldberg et al. |
| 6,355,431 B1 | 3/2002 | Chee et al. |
| 6,419,949 B1 | 7/2002 | Gasco |
| 6,428,752 B1 | 8/2002 | Montagu |
| 6,482,591 B2 | 11/2002 | Lockhart et al. |
| 6,489,606 B1 | 12/2002 | Kersey et al. |

(Continued)

FOREIGN PATENT DOCUMENTS
WO    WO 93/017126    9/1993
(Continued)

OTHER PUBLICATIONS

Ausubel et al., *Current Protocols in Molecular Biology*, John Wiley and Sons, Baltimore, MD, (2002) Cover and copyright page only.
Beaucage et al., "The Functionalization of Oligonucleotides Via Phosphoramidite Derivatives," *Tetrahedron* 49(10):1925 (1993).
Bettuzzi et al., "Successful prediction of prostate cancer recurrence by gene profiling in combination with clinical data: a 5-year follow-up study," *Cancer Res.* 63:3469-3472 (2003).
Bibikova et al., "Gene expression profiles in formalin-fixed, paraffin-embedded tissues obtained with a novel assay for microarray analysis," *Clin. Chem.* 50:2384-2386 (2004).
Bibikova et al., "High-throughput DNA methylation profiling using universal bead arrays," *Genome Res.* 16:383-393 (2006).
Bibikova et al., "Quantitative gene expression profiling in formalin-fixed, paraffin-embedded tissues using universal bead arrays," *Am. J. Pathol.* 165:1799-1807 (2004).
Brill et al., "Synthesis of of oligodeoxynucleoside phosphorodithioates via thioamidites", *J. Am. Chem. Soc.*, 111:2321-2322 (1989).
Butte, "The use and analysis of microarray data," *Nature Reviews Drug Discov.* 1:951-960 (2002).

(Continued)

*Primary Examiner* — James Martinell
(74) *Attorney, Agent, or Firm* — Jones Day

(57) ABSTRACT

The present invention provides a method for preparing a reference model for cancer relapse prediction that provides higher resolution grading than Gleason score alone. The method encompasses obtaining from different individuals a plurality of prostate carcinoma tissue samples of known clinical outcome representing different Gleason scores; selecting a set of signature genes having an expression pattern that correlates positively or negatively in a statistically significant manner with the Gleason scores; independently deriving a prediction score that correlates gene expression of each individual signature gene with Gleason score for each signature gene in said plurality of prostate carcinoma tissue samples; deriving a prostate cancer gene expression (GEX) score that correlates gene expression of said set of signature genes with the Gleason score based on the combination of independently derived prediction scores in the plurality of prostate cancer tissue samples; and correlating said GEX score with the clinical outcome for each prostate carcinoma tissue sample. A set of signature genes is provided that encompasses all or a sub-combination of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B, and PROK1. Also provided a methods for predicting the probability of relapse of cancer in an individual and methods for deriving a prostate cancer gene expression (GEX) score for a prostate carcinoma tissue sample obtained from an individual.

22 Claims, 9 Drawing Sheets

U.S. PATENT DOCUMENTS

| | | | |
|---|---|---|---|
| 6,514,751 | B2 | 2/2003 | Johann et al. |
| 6,524,793 | B1 | 2/2003 | Chandler et al. |
| 6,770,441 | B2 | 8/2004 | Dickinson et al. |
| 6,859,570 | B2 | 2/2005 | Walt et al. |
| 6,949,342 | B2 | 9/2005 | Golub et al. |
| 7,106,513 | B2 | 9/2006 | Moon et al. |
| 7,126,755 | B2 | 10/2006 | Moon et al. |
| 7,164,533 | B2 | 1/2007 | Moon et al. |
| 7,501,248 | B2 | 3/2009 | Golub et al. |
| 2002/0006617 | A1 | 1/2002 | Fan et al. |
| 2002/0132241 | A1 | 9/2002 | Fan et al. |
| 2003/0036064 | A1 | 2/2003 | Stuelpnagel et al. |
| 2003/0108900 | A1 | 6/2003 | Oliphant et al. |
| 2003/0170684 | A1 | 9/2003 | Fan |
| 2003/0211489 | A1 | 11/2003 | Shen et al. |
| 2003/0215821 | A1 | 11/2003 | Gunderson et al. |
| 2003/0215827 | A1 | 11/2003 | Yue et al. |
| 2004/0018491 | A1 | 1/2004 | Gunderson et al. |
| 2004/0121364 | A1 | 6/2004 | Chee et al. |
| 2004/0259105 | A1 | 12/2004 | Fan et al. |
| 2005/0142573 | A1 | 6/2005 | Glinskii |
| 2005/0181394 | A1 | 8/2005 | Steemers et al. |
| 2005/0227252 | A1 | 10/2005 | Moon et al. |
| 2005/0260664 | A1 | 11/2005 | Shaughnessy et al. |
| 2006/0006327 | A1 | 1/2006 | Donaldson et al. |
| 2006/0023310 | A1 | 2/2006 | Putnam et al. |
| 2006/0071075 | A1 | 4/2006 | Moon et al. |
| 2006/0119913 | A1 | 6/2006 | Moon |
| 2006/0195266 | A1 | 8/2006 | Yeatman |
| 2007/0099197 | A1 | 5/2007 | Afar et al. |
| 2007/0220621 | A1 | 9/2007 | Clarke et al. |

FOREIGN PATENT DOCUMENTS

| | | |
|---|---|---|
| WO | WO/95/35505 | 12/1995 |
| WO | WO 00/063437 | 10/2000 |
| WO | WO 2004/024328 | 3/2004 |
| WO | WO 2005/033681 | 4/2005 |

OTHER PUBLICATIONS

Carlsson et al., "Screening for genetic mutations," *Nature* 380:207 (1996).

De Mesmaeker et al., "Comparison of Rigid and Flexible Backbones in Antisense Oligonucleotides", *Bioorg. Medic. Chem. Lett.*, 4(3):395-398 (1994).

Dempcy et al., "Synthesis of a thymidyl pentamer of deoxyribonucleic guanidine and binding studies with DNA homopolynucleotides," *Proc. Natl. Acad. Sci. USA* 92:6097-6101 (1995).

Dhanasekaran et al., "Delineation of prognostic biomarkers in prostate cancer," *Nature* 412:822-826 (2001).

Egholm, "Oligonucleotide Analogues with an Achiral Peptide Backbone," *J. Am. Chem. Soc.* 114:1895-1897 (1992).

Egholm, et al., "PNA hybridizes to complementary oligonucleotides obeying the Watson-Crick hydrogen-bonding rules," *Nature*, 365:566 (1993).

Fan et al., "A versatile assay for high-throughput gene expression profiling on universal array matrices," *Genome Res.* 14:878-885 (2004).

Fan et al., "Highly parallel SNP genotyping," *Cold Spring Harbor Symposia Quant. Biol.* 68:69-78 (2003).

Febbo and Sellers et al., "Use of expression analysis to predict outcome after radical prostatectomy," *J. Urol.* 170:S11-19, discussion S19-20 (2003).

Galinsky, "Automatic registration of microarray images. II. Hexagonal grid," *Bioinformatics* 19:1832-1836 (2003).

Glinsky et al., "Gene expression profiling predicts clinical outcome of prostate cancer," *J. Clin. Invest.* 113:913-923 (2004).

Godfrey et al., "Quantitative mRNA expression analysis from formalin-fixed, paraffin-embedded tissues using 5' nuclease quantitative reverse transcription-polymerase chain reaction," *J. Mol. Diagnostics*, 2:84-91 (2000).

Goldsworthy et al., "Effects of fixation on RNA extraction and amplification from laser capture microdissected tissue," *Mol. Carcinog.* 25:86-91 (1999).

Gunderson et al., "A genome-wide scalable SNP genotyping assay using microarray technology," *Nat. Genet.* 37:549-554 (2005).

Gunderson et al., "Decoding randomly ordered DNA arrays," *Genome Res.* 14:870-877 (2004).

Henshall et al., "Survival analysis of genome-wide gene expression profiles of prostate cancers identifies new prognostic targets of disease relapse," *Cancer Res.* 63:4196-4203 (2003).

Horn et al., "Oligonucleotides with alternating anionic and cationic phosphoramidate linkages: Synthesis and hybridization of stereouniform isomers," *Tetrahedron Lett.* 37:743-746 (1996).

Jackson et al., "Detection of measles virus RNA in paraffin-embedded tissue," *Lancet* 1(8651):1391 (1989).

Jackson et al., "Tissue extraction of DNA and RNA and analysis by the polymerase chain reaction," *J. Clin. Pathol.* 43:499-504 (1990).

"Unusual conformation of a 3'-thioformacetal linkage in a DNA duplex," *J. Biomolecular NMR* 34:17 (1994), Gao et al.

Jenkins et al., "The biosynthesis of carbocyclic nucleosides," *Chem. Soc. Rev.* 24:169-176 (1995).

Jung et al., "Hybridization of alternating cationic/anionic oligonucleotides to rna segments," Nucleosides & Nucleotides 13: 1597-1605 (1994).

Kuhn et al., "A novel, high-performance random array platform for quantitative gene expression profiling," *Genome Res.* 14:2347-2356 (2004).

Lapointe et al., "Gene expression profiling identifies clinically relevant subtypes of prostate cancer," *Proc. Natl. Acad. Sci. USA* 101:811-816 (2004).

Letsinger, "Phosphoramidate analogs of oligonucleotides," *J. Org. Chem.* 35:3800-3803 (1970).

Lossos et al., "Prediction of survival in diffuse large-B-cell lymphoma based on the expression of six genes," *N. Engl. J. Med.* 350:1828-1837 (2004).

Luo et al., "Gene expression signature of benign prostatic hyperplasia revealed by cDNA microarray analysis," *Prostate* 51:189-200 (2002).

Mag et al., "Synthesis and selective cleavage of an oligodeoxynucleotide containing a bridged internucleotide 5'-phosphorothioate linkage," *Nucleic Acids Res.* 19:1437-1441 (1991).

Meier et al., "Peptide Nucleic Acids (PNAs)-Unusual Properties of Nonionic Oligonucleotide Analogues," *Angew Chem. Int. Ed. Engl.*, 31:1008-1010 (1992).

Michael et al., "Randomly ordered addressable high-density optical sensor arrays," *Anal. Chem.* 70:1242-1248 (1998).

Miller, et al., eds., *Gene Transfer Vectors for Mammalian Cells*, Cold Spring Harbor Laboratory Press, Cold Spring Harbor, NY (1987).

Nelson et al., "Prostate cancer," *N. Engl. J. Med.* 349:366-381 (2003).

Phillips and Eberwine, "Antisense RNA Amplification: A Linear Amplification Method for Analyzing the mRNA Population from Single Living Cells," *Methods* 10:283-288 (1996).

Ramaswamy et al., "A molecular signature of metastasis in primary solid tumors," *Nat. Genet.* 33:49-54 (2003).

Ramaswamy et al., "DNA microarrays in clinical oncology," *J. Clin. Oncol.* 20:1932-1941 (2002).

Ramaswamy, "Translating cancer genomics into clinical oncology," *N. Engl. J. Med.* 350:1814-1816 (2004).

Rawls, "Reproductive hazards in the workplace," *Chem. Eng. News* 58(7):35-37 (1980).

Sambrook et al., *Molecular Cloning : A Laboratory Manual*, 3rd edition, Cold Spring Harbor Laboratory, Cold Spring Harbor, NY, (1989) Cover and copyright page only.

Sanghui and Cook, eds., ASC Symposium Series 580, chapters 2 and 3, "Carbohydrate Modifications in Antisense Research".

Sanghui and Cook, eds., ASC Symposium Series 580, Chapters 6 and 7, "Carbohydrate Modifications in Antisense Research".

Sawai, "Synthesis and properties of oligoadenylic acids containing 2'-5' phosphoramide linkage," *Chem. Lett.* 805-808 (1984).

Singh et al., "Gene expression correlates of clinical prostate cancer behavior," *Cancer Cell* 1:203-209 (2002).

Specht et al., "Quantitative gene expression analysis in microdissected archival formalin-fixed and paraffin-embedded tumor tissue," *Am. J. Pathol.* 158:419-429 (2001).

Specht et al., "Quantitative gene expression analysis in microdissected archival tissue by real-time RT-PCR," *J. Mol. Med.* 78:B27 (2000).

Sprinzl et al., "Enzymatic incorporation of ATP and CTP analogues into the 3' end of tRNA," *Eur. J. Biochem.* 81:579-589 (1977).

Stamey et al., "Molecular genetic profiling of Gleason grade 4/5 prostate cancers compared to benign prostatic hyperplasia," *J. Urol.* 166:2171-2107 (2001).

Steinbrecher, "Targeted Inactivation of the Mouse Guanylin Gene Results in Altered Dynamics of Colonic Epithelial Proliferation," *Am. J. of Pathol.* 161: 2169-2178 (2002).

Stuart et al., "In silico dissection of cell-type-associated patterns of gene expression in prostate cancer," *Proc. Natl. Acad. Sci. USA* 101:615-620 (2004).

Sullivan Pepe et al. "Phases of biomarker development for early detection of cancer," *J. Natl. Cancer Inst.* 93:1054-1061 (2001).

TTABPW Group, "Expression profiling—best practices for data generation and interpretation in clinical trials," *Nat. Rev. Genet.* 5:229-237 (2004).

Van 'T Veer et al., "Gene expression profiling predicts clinical outcome of breast cancer," *Nature* 415:530-536 (2002).

Van De Vijver et al., "A gene-expression signature as a predictor of survival in breast cancer," *N. Engl. J. Med.* 347:1999-2009 (2002).

Von Kiedrowski et al., "Parabolic Growth of a Self-Replicating Hexadeoxynucleotide Bearing a 3'-5'-Phosphoamidate Linkage," *Angew. Chem. Intl. Ed. English* 30(4):423-426 (1991).

Walt, "Techview: molecular biology. Bead-based fiber-optic arrays," *Science* 287:451-452 (2000).

Weir and Blackwell, eds., *Handbook of Experimental Immunology*, 4th Ed., Blackwell Science Inc., Cambridge, MA (Jun. 1987).

Welsh et al., "Analysis of gene expression identifies candidate markers and pharmacological targets in prostate cancer," *Cancer Res.* 61:5974-5978 (2001).

Yeakley et al., "Profiling alternative splicing on fiber-optic arrays," *Nat. Biotechnol.* 20:353-358 (2002).

Eckstein et al., "Oligonucleotides and Analogues—A Practical Approach," NY, Oxford Univ. Press, 1991, Contents ix-xvii.

Finke et al., "An Improved Strategy and a Useful Housekeeping Gene for RNA Analysis from Formalin-Fixed, Paraffin-Embedded Tissues by PCR," *BioTechniques*, 14(3)448-453 (1993).

Gao and Jeffs, "Unusual conformation of a 3'-thioformacetal linkage in a DNA duplex," *J. Biomol. NMR*, 4:17-34(1994).

Latil et al., "Gene Expression Profiling in Clinically Localized Prostate Cancer: A Four-Gene Expression Model Predicts Clinical Behavior," *Clin. Cancer Res.*, 9:5477-5485 (2003).

Letsinger et al., "Cationic Oligonucleotides," *J. Am. Chem.Soc.*, 110:4470-4471 (1988).

Letsinger et al., "Effects of pendant groups at phosphorus on binding properties of d-ApA analogues," *Nucleic Acids Res.*, 14(8): 3487-3499 (1986).

Pauwels et al., "Biological Activity of New 2-5A Analogues," *Chemica Scripta*, 26:141-145 (1986).

Stanta and Bonin, "RNA Quantitative Analysis from Fixed and Paraffin-Embedded Tissues: Membrane Hybridization and Capillary Electrophoresis." *BioTechniques*, 24(2):271-276 (1998).

Stanta et al., "RNA Extracted from Paraffin-Embedded Human Tissues is Amenable to Analysis by PCR Amplification," *BioTechniques*, 11(3):304-308 (1991).

Stanta et al., "RNA Extraction from Formalin-Fixed and Paraffin-Embedded Tissues," *Meth. in Mol. Biol.*, 86: 23-26 (1998).

GENE EXPRESSION PROFILES TO PREDICT RELAPSE OF PROSTATE CANCER

FIELD OF THE INVENTION

This application claims the benefit of priority of U.S. Provisional application Ser. No. 60/787,868, filed Mar. 31, 2006, the entire contents of which are incorporated herein by reference.

This invention relates generally to gene expression profiling and, more specifically, to relapse prediction and clinical management of prostate cancer.

BACKGROUND OF THE INVENTION

Prostate cancer is the most common cancer in American men and is the second leading cause of cancer death. Progress in treating human prostate cancer has been hampered by the finding that histologically identical cancers can exhibit widely variant clinical behavior. For example, in some men diagnosed with prostate cancer, the disease progresses slowly with a prolonged natural history while in other patients, disease progression can be rapid and definitive local therapy can be ineffective. The uncertainty regarding the appropriate clinical management of prostate cancer in many patients is related to an incomplete and unclear understanding of the molecular and genetic changes involved in prostate cancer development and disease progression.

A variety of clinical models or nomograms have been developed to aid clinicians with pre-treatment risk assessment. For example, since 1988, the routine use of serum prostate-specific antigen (PSA) testing in men at risk for prostate cancer has led to more favorable disease characteristics at presentation (stage migration) and earlier diagnosis and treatment. Several investigators have used these clinical parameters to stratify patients into risk groups (low, intermediate, high) and to predict clinical outcomes (Nomograms). Despite these useful parameters, approximately 30% of patients with intermediate-risk prostate cancer fail standard treatment as evidenced by a rising serum PSA following definitive therapy. A better understanding of the molecular abnormalities that define these tumors at high risk for relapse is needed to help identify more precise biosignatures.

For patients newly diagnosed with prostate cancer, there are three well-defined predictors of disease extent and outcome following treatment. These factors are clinical tumor stage (T1-T4) by digital rectal examination, Gleason score of the diagnostic biopsy specimen and serum PSA level. However, each of these factors alone has not proven definitive in predicting disease extent and outcome for an individual patient. Clinical staging by digital rectal examination may underestimate the presence of extracapsular disease extension in 30-50% of patients. Although biopsy Gleason score may be helpful in predicting pathologic stage and outcome following treatment at either end of the spectrum (i.e. Gleason 2-4 or Gleason 8-10 tumors), it is not as helpful for the majority of patients who present with Gleason 5-7 disease. As risk assessment for patients newly diagnosed with prostate cancer continues to evolve, newer tools, such as genetic or molecular determinants are needed to better predict the behavior of an individual tumor.

A need exists for large-scale discovery, validation, and clinical application of mRNA biosignatures of disease and for methods of genomic analysis in patients with established clinical prostate cancer disease to predict disease outcomes. The present invention satisfies this need and provides related advantages as well.

SUMMARY OF THE INVENTION

The present invention provides a method for preparing a reference model for cancer relapse prediction that provides higher resolution grading than Gleason score alone. The method encompasses obtaining from different individuals a plurality of prostate carcinoma tissue samples of known clinical outcome representing different Gleason scores; selecting a set of signature genes having an expression pattern that correlates positively or negatively in a statistically significant manner with the Gleason scores; independently deriving a prediction score that correlates gene expression of each individual signature gene with Gleason score for each signature gene in said plurality of prostate carcinoma tissue samples; deriving a prostate cancer gene expression (GEX) score that correlates gene expression of said set of signature genes with the Gleason score based on the combination of independently derived prediction scores in the plurality of prostate cancer tissue samples; and correlating said GEX score with the clinical outcome for each prostate carcinoma tissue sample. A set of signature genes is provided that encompasses all or a sub-combination of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B, and PROK1. Also provided are methods for predicting the probability of relapse of cancer in an individual and methods for deriving a prostate cancer gene expression (GEX) score for a prostate carcinoma tissue sample obtained from an individual.

Numbers in red identify samples with poor performance.

Figure 7:
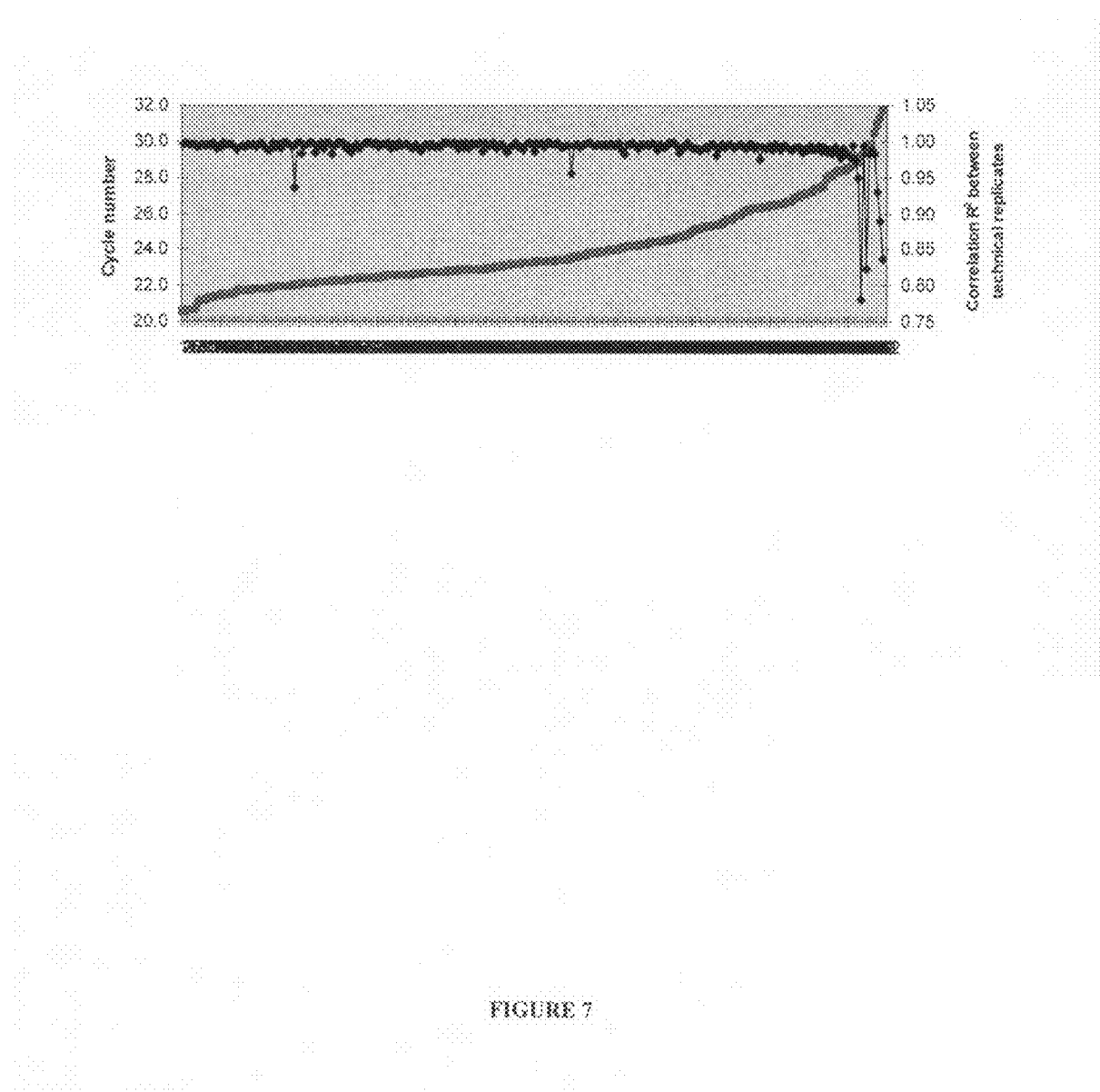

FIG. 7 shows sample QC (by qPCR) and array data quality assessment. Highly reproducible gene expression data are obtained with samples that have up to 8 cycle difference in qPCR (i.e. ~170-fold difference in "PCR-able" RNA input) for a housekeeping gene RPL13A. Samples are pre-qualified for array analysis by qPCR, using a Ct number of 28 as the cutoff.

Figure 8:
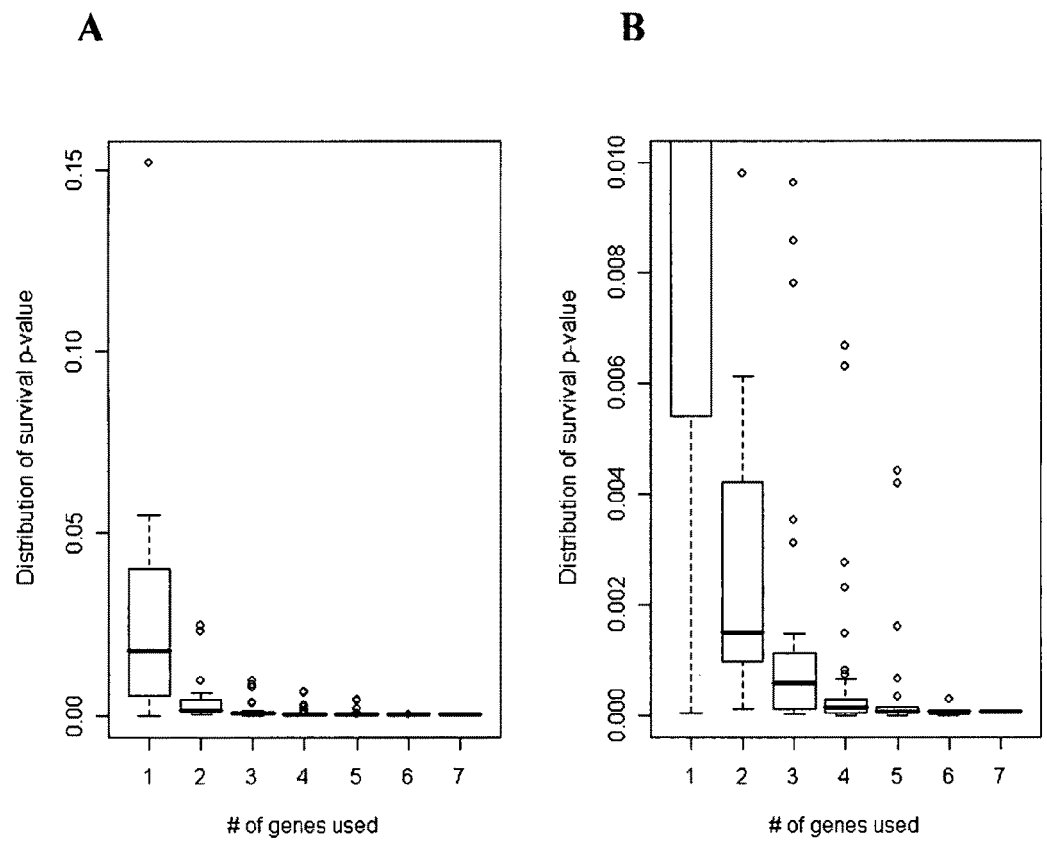

FIG. 8 shows a plot of the distribution of survival p-values for various collections of signature genes selected among the following 7 genes: MKI67, GI_2094528, HOXC6, CCK, memD, FBP1, and CDC6. The same data is plotted in panels A and B but displayed with different scale on the y axis.

Figure 9:
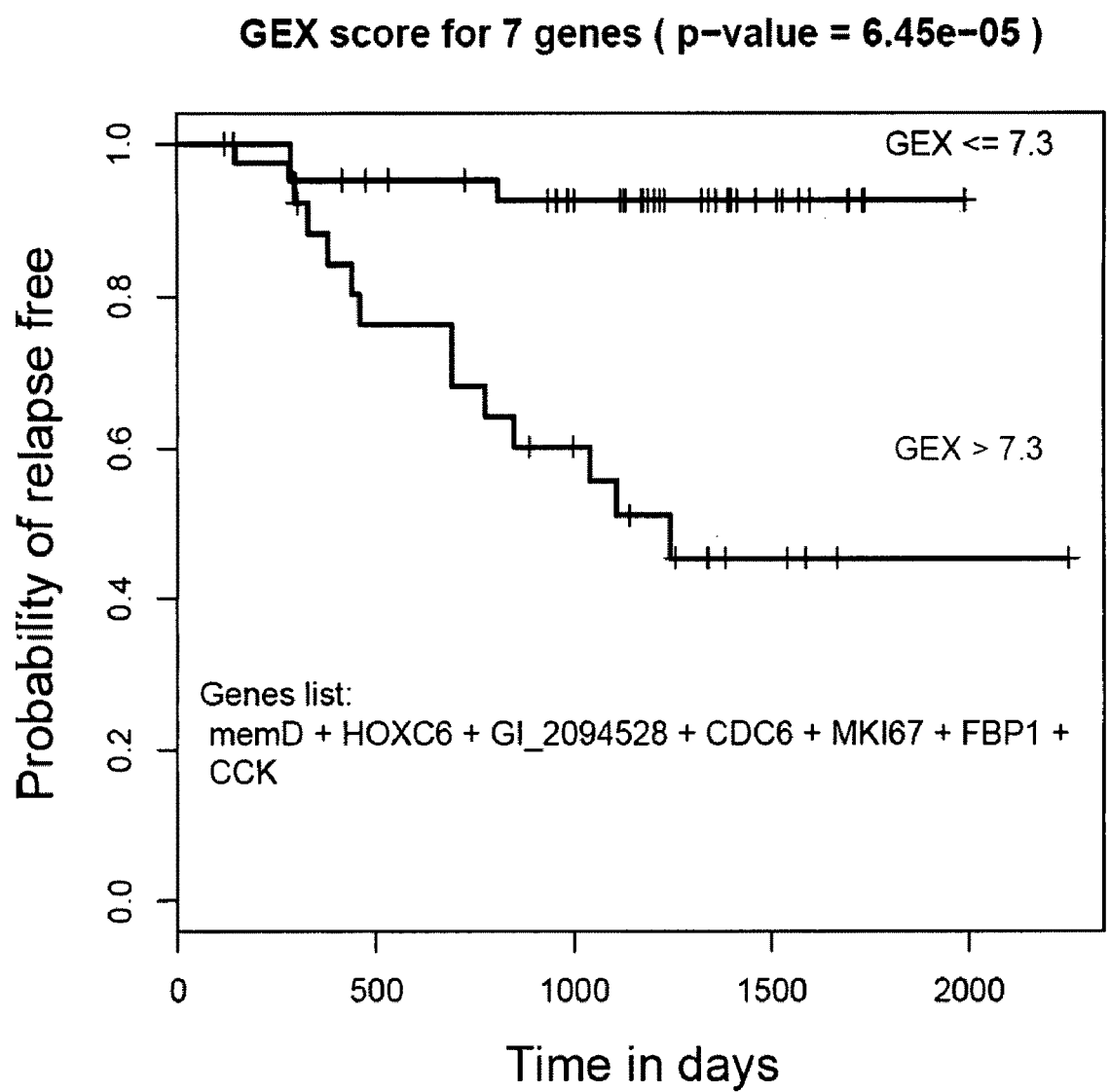

FIG. 9 shows Kaplan-Maier analysis of relapse (N=71) based on the GEX score derived from the following 7 genes: MKI67, GI_2094528, HOXC6, CCK, memD, FBP1, and CDC6. X-axis: Time to relapse (days); Y-axis: Relapse free probability.

DETAILED DESCRIPTION OF THE INVENTION

This invention is directed to methods for gene expression profiling in cancer tissues and the identification of cancer diagnostic and prognostic biomarkers. In particular, the method of the invention allows for the establishment of a molecular signature based on identifying a correlation between the gene expression of each member of a set of signature genes in a cell population derived from prostate carcinoma tissue sample with the Gleason score corresponding to the tissue sample. It has been discovered that the molecular signature can be expressed as a combined score, termed the Gene Expression Score ("GEX score"), which allows for relapse prediction more sensitive than relapse prediction based solely on Gleason score. For each member of the set of signature genes that contribute to the GEX score, a highly reproducible correlation of gene expression, either positive or negative, with Gleason score can reproducibly be calculated and incorporated into the GEX score.

The present invention provides a method for establishing a model, also referred to as a "reference model," for prostate relapse prediction against which any individual patient sample can be compared to predict relapse probability more accurately than Gleason score alone. The invention also provides a method for deriving a prostate cancer gene expression score by obtaining a cell population from a tissue sample obtained from an individual, calculating the GEX score in the tissue sample, and comparing the GEX score to an established model for relapse prediction. The invention also provides a set of signature genes for prostate cancer relapse prediction.

In a particular embodiment, the invention provides a method for preparing a model for cancer relapse prediction. This method comprises the following steps: (a) obtaining a plurality of cell populations from prostate carcinoma tissues representing different Gleason scores, wherein the clinical outcome corresponding to each of the prostate carcinoma tissues is known; (b) selecting a set of signature genes having an expression pattern that correlates positively or negatively with the Gleason scores in prostate cancer patients; (c) statistically deriving a prediction score for each signature gene in the plurality of cell populations, wherein the prediction score correlates gene expression of each individual signature gene with Gleason score; (d) statistically deriving a prostate cancer gene expression score by calculating the average of the independently derived prediction scores in the plurality of tissue samples, wherein the prostate cancer gene expression score correlates gene expression of the set of signature genes with the Gleason score; and (e) establishing a model for relapse prediction from the plurality of cell populations that describes the association between gene expression score and probability of relapse for prostate cancer.

In a particular embodiment, the invention provides a method for predicting the probability of relapse of prostate cancer in an individual by performing the steps of (a) providing expression levels for a collection of signature genes from a test individual; (b) deriving a score that captures the expression levels for the collection of signature genes; (c) providing a model comprising information correlating the score with prostate cancer relapse; and (d) comparing the score to the reference model, thereby determining the probability of prostate cancer relapse for the individual.

Signature genes of the invention, which are differentially expressed within prostate carcinomas and which are further positively or negatively correlated with Gleason score, are as follows: GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B, and PROK1. Of the 21 signature genes, twelve are positively correlated with Gleason score: GI_2094528, CCNE2, CDC6, FBP1, HOXC6, MKI67, MYBL2, PTTG1, RAMP, UBE2C, Wnt5A, MEMD; and nine are negatively correlated with Gleason score: KIP2, NRG1, NBL1, Prostein, AZGP1, CCK, MLCK, PPAP2B, and PROK1.

The sensitivity and specificity of the molecular signature derived from these 21 signature genes, or subset thereof, has utility for patients undergoing prostate biopsy for diagnosis of carcinoma based on applicability of the methods described herein to diagnosis as well as prognosis through biopsy samples. Furthermore, the present invention enables the development of a diagnostic test that is technically simple and applicable for routine clinical use, and incorporation into existing prostate cancer nomograms (Group TTABPW, *Nat Rev Genet* 5:229-37 (2004); Ramaswamy, *N Engl J Med* 350:1814-6 (2004); Sullivan Pepe et al. *J Natl Cancer Inst* 93:1054-61 (2001)).

The articles "a" and "an" are used herein to refer to one or to more than one (i.e. to at least one) of the grammatical object of the article. By way of example, "an element" means one element or more than one element, unless explicitly indicated to the contrary.

"Prostate cancer" as used herein includes carcinomas, including, carcinoma in situ, invasive carcinoma, metastatic carcinoma and pre-malignant conditions.

As used herein the term "comprising" means that the named elements are essential, but other signature genes or claim elements may be added and still represent a composition or method within the scope of the claim. The transitional phrase "consisting essentially of" means that the claimed composition or method encompasses additional elements, including, for example, additional signature genes, that do not affect the basic and novel characteristics of the claimed invention. The transitional phrase "comprising essentially" means that the claimed composition or method encompasses additional elements, including, for example, additional signature genes or claim, that do not substantially affect the basic and novel characteristics of the claimed invention.

As used herein, the term "signature gene" refers to a gene whose expression is correlated, either positively or negatively, with disease extent or outcome or with another predictor of disease extent or outcome. A gene expression score (GEX) can be statistically derived from the expression levels of a set of signature genes and used to diagnose a condition or to predict clinical course. A "signature nucleic acid" is a nucleic acid comprising or corresponding to, in case of cDNA, the complete or partial sequence of a RNA transcript encoded by a signature gene, or the complement of such complete or partial sequence. A signature protein is encoded by or corresponding to a signature gene of the invention.

The term "relapse prediction" is used herein to refer to the prediction of the likelihood of cancer recurrence in patients with no apparent residual tumor tissue after treatment. The predictive methods of the present invention can be used clinically to make treatment decisions by choosing the most appropriate treatment modalities for any particular patient. The predictive methods of the present invention also can provide valuable tools in predicting if a patient is likely to respond favorably to a treatment regimen, such as surgical intervention, chemotherapy with a given drug or drug combination, and/or radiation therapy.

In the exemplified embodiments relating to cancer relapse prediction, the gene expression of 21 signature genes, or subsets thereof, differentially expressed in prostate cancer is correlated to Gleason scores. The Gleason grading system is based on the glandular pattern of the tumor. Gleason grade takes into account the ability of the tumor to form glands. A pathologist, using relatively low magnification, performs the histologic review necessary for assigning the Gleason grade. The range of grades is 1-5: 1, 2 and 3 are considered to be low to moderate in grade; 4 and 5 are considered to be high grade. The prognosis for a given patient generally falls somewhere between that predicted by the primary grade and a secondary grade given to the second most prominent glandular pattern. When the two grades are added the resulting number is referred to as the Gleason score. The Gleason Score is a more accurate predictor of outcome than either of the individual grades. Thus, the traditionally reported Gleason score will be the sum of two numbers between 1-5 with a total score from 2-10. It is unusual for the primary and secondary Gleason grade to differ by more than one, such that the only way that there can be a Gleason score 7 tumor is if the primary or secondary Gleason grade is 4. Because of the presence of grade 4 glandular patterns in tissue having Gleason score 7, these tumors can behave in a much more aggressive fashion than those having Gleason score 6. In a recent study of over 300 patients, the disease specific survival for Gleason score 7 patients was 10 years. In contrast, Gleason score 6 patients survived 16 years and Gleason 4-5 for 20 years. It is therefore clear that the prognosis for men with Gleason score 7 tumors is worse than for men with Gleason score 5 and 6 tumors. Under certain circumstances it is suggested that men with Gleason 7 tumors can be considered for clinical trials.

As disclosed herein, the gene expression score (GEX) derived from the expression levels of signature genes can be used to predict relapse of prostate cancer. A "GEX score" or "score" is a value that captures the expression levels for a collection of signature genes. Notably, making continuous analogy of Gleason score increased molecular resolution, especially at a Gleason Score between 7 and 8, in which relapse probability of patients can be stratified beyond the capability of the Gleason score alone because the GEX score provides a more sensitive predictor of relapse for prostate cancer, especially in this range. As disclosed in Example I below, a significant difference exists in the mean of the GEX score between GS7 patients who had relapse (GS7-Y) and those without relapse (GS7-N), making the GEX score a valuable source of information for the very patients faced with the most critical decision point along the Gleason score spectrum.

Furthermore, while it is established that Gleason score 7 tumors behave in a more aggressive fashion than do Gleason 5 and 6 tumors, it has been less clear whether or not it makes a difference if the primary or secondary pattern accounts for the Gleason score 4 grade. Some studies have shown Gleason 4+3 to be a worse prognostic sign than is Gleason 3+4 (where Gleason x+y represents Gleason score derived from primary grade "x" and secondary grade "y"). However, this has not always been the case and there are studies that find no difference between the two scores. To date, there had not been a prospective study that has attempted to answer this question and it has remained a controversial point. The present invention confirms that among Gleason score 7 patients, a primary Gleason score of 4 is consistent with a significantly higher relapse probability. Among the GS7 patients, 21 are (3+4) and 11 are (4+3), of which 1 and 4 are relapsed respectively (Exact Fisher test p=0.037). A mean GEX score of 7.236 and 7.305 for the two groups, respectively (p=0.071 for hypothesis testing increased GEX score for 4+3 patients) was obtained.

The ability to stratify individuals having a Gleason Score between 7 and 8 based on probability of relapse is significant because a Gleason score of 7 is a crucial decision point that necessitates seeking treatment as early as possible, considering therapies beyond surgery and radiation, and having frequent follow-ups.

Among the signature genes disclosed herein is MEMD, a cell adhesion molecule often found in metastasizing human melanoma cell lines. The intact cell adhesion function of MEMD can both favor primary tumor growth and represent a rate-limiting step for tissue invasion from vertical growth phase melanoma. Over expression of this molecule is associated with tumor invasion and nodal metastasis in esophageal squamous cell carcinoma. MEMD expression is up-regulated in low-grade prostate tumors and down-regulated in high-grade tumors and can play role in progression of prostate cancer. Also among the signature genes, HOXC6 was identified as a good signature for prediction of prostate cancer patient outcome, as was UBE2C, ubiquitin-conjugating enzyme E2C, which is highly expressed in various human primary tumors (e.g. anaplastic thyroid carcinomas) and has an ability to promote cell growth and malignant transformation. WNT5A: wingless-type MMTV integration site family, member 5A. The WNT gene family consists of structurally related genes which encode secreted signaling proteins, which have been implicated in oncogenesis and in several developmental processes, including regulation of cell fate and patterning during embryogenesis. Wnt-5a serves as an antagonist to the canonical Wnt-signaling pathway with tumor suppressor activity in differentiated thyroid carcinomas and is involved in the response of malignant neuroblasts to retinoic acid. Up-regulation of Wnt-5a is a signature of the malignant phenotype of human squamous cell carcinoma and frequent up-regulation exists of WNT5A mRNA in primary gastric cancer. Increased expression of WNT5a is associated with cell motility and invasion of metastatic melanoma. The gene product of a further signature gene, PTTG1: pituitary tumor-transforming 1 has transforming activity in vitro and tumorigenic activity in vivo, and the gene is highly expressed in various tumors.

The invention also provides a collection of isolated prostate cancer signature genes consisting essentially of CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes consisting of CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, FBP1, HOXC6, MKI67, MYBL2, PTTG1, RAMP, UBE2C, Wnt5A, MEMD, AZGP1, CCK, MLCK, PPAP2B and PROK1.

The invention also provides a collection of isolated prostate cancer signature genes consisting essentially of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes consisting of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1.

The invention also provides a collection of isolated prostate cancer signature genes comprising any subset of the 21 genes set forth above including, for example, at least 1, 2, 3, 4, 5, 6, 7, 8, 9, 10, 11, 12, 13, 14, 15, 16, 17, 18, 19, or 20 of the 21 genes. The invention also provides a collection of isolated prostate cancer signature genes comprising CCNE2, CDC6, FBP1, HOXC6, MKI67, MYBL2, PTTG1, RAMP, UBE2C, Wnt5A, MEMD, AZGP1, CCK, MLCK and PPAP2B. The invention also provides a collection of isolated prostate cancer signature genes comprising CCNE2, CDC6, FBP1, HOXC6, MKI67, MYBL2, PTTG1, RAMP, UBE2C, Wnt5A, MEMD, AZGP1, CCK, and PROK1. The invention also provides a collection of isolated prostate cancer signature genes comprising CCNE2, CDC6, FBP1, HOXC6, MKI67, MYBL2, PTTG1, RAMP, UBE2C, Wnt5A, MEMD, AZGP1, MLCK, and PPAP2B. The invention also provides a collection of isolated prostate cancer signature genes comprising CCNE2, CDC6, FBP1, HOXC6, MKI67, MYBL2, PTTG1, RAMP, UBE2C, Wnt5A, MEMD, CCK, MLCK, PPAP2B and PROK1. The invention also provides a collection of isolated prostate cancer signature genes comprising CCNE2, CDC6, FBP1, HOXC6, MKI67, MYBL2, PTTG1, RAMP, UBE2C, Wnt5A, AZGP1, CCK, MLCK, PPAP2B and PROK1. The invention also provides a collection of isolated prostate cancer signature genes comprising CCNE2, CDC6, FBP1, HOXC6, MKI67, MYBL2, PTTG1, RAMP, UBE2C, MEMD, AZGP1, CCK, MLCK, PPAP2B and PROK1. The invention also provides a collection of isolated prostate cancer signature genes comprising CCNE2, CDC6, FBP1, HOXC6, MKI67, MYBL2, PTTG1, RAMP, Wnt5A, MEMD, AZGP1, CCK, MLCK, PPAP2B and PROK1. The invention also provides a collection of isolated prostate cancer signature genes comprising CCNE2, CDC6, FBP1, HOXC6, MKI67, MYBL2, PTTG1, UBE2C, Wnt5A, MEMD, AZGP1, CCK, MLCK, PPAP2B and PROK1. The invention also provides a collection of isolated prostate cancer signature genes comprising CCNE2, CDC6, FBP1, HOXC6, MKI67, MYBL2, RAMP, UBE2C, Wnt5A, MEMD, AZGP1, CCK, MLCK, PPAP2B and PROK1. The invention also provides a collection of isolated prostate cancer signature genes comprising CCNE2, CDC6, FBP1, HOXC6, MKI67, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, FBP1, HOXC6, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, FBP1, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, CDC6, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CCNE2, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated prostate cancer signature genes comprising CDC6, FBP1, HOXC6, MKI67, MYBL2, PTTG1, RAMP, UBE2C, Wnt5A, MEMD, AZGP1, CCK, MLCK, PPAP2B and PROK1. All of the signature genes can be present in "isolated" form.

One skilled in the art can readily determine other combinations of signature genes sufficient to practice the inventions claimed herein. For example, based on the Pearson's correlation coefficient shown in Table 2 or Table 4, one skilled in the art can readily determine a sub-combination of prostate cancer signature genes suitable for methods of the invention. Those exemplary genes having lowest correlation can be excluded, with the remaining genes providing a sufficient collection of isolated prostate cancer signature genes suitable for relapse prediction of prostate cancer. For example, of those genes having a negative correlation, the CCK gene has the lowest correlation, and therefore removing the CCK gene is expected to have the least effect on overall accuracy of the GEX score. Similarly, of those genes having a positive correlation, removing the UBE2C is expected to have the least effect on overall accuracy of the GEX score. One skilled in the art can readily recognize these or other appropriate genes that can be omitted from the 21 identified prostate cancer signature genes and still be sufficient for methods of the invention.

Alternatively, one skilled in the art can remove any one or a few of the 21 identified prostate cancer signature genes so long as those remaining provide a sufficient statistical correlation for use in methods of the invention. Exemplary collections of prostate cancer signature genes include, for example, those set forth above and in the Examples. It is readily recognized by one skilled in the art that these listed combinations are merely exemplary and that any of a number of such combinations can readily be determined by one skilled in the art. For example, a sub-combination can be selected by removing the signature gene(s) with the weakest correlation, for example, GI_2094528, NRG1, Prostein or UBE2C based on overall correlation, including positive and negative; NRG1, Prostein or CCK based on the weakest negative correlation of the five signature genes having a negative correlation with GS. HOXC6 and RAMP have the strongest and second strongest, respectively, correlation to GS score of the sixteen signature genes and can therefore be included in a sub-combination based on this statistic. However, it is understood that, given the set of 21 signature genes, removal of a signature gene having a strong correlation, will likely not have a big impact on the overall GEX score. The correlations are set forth in Tables 2 and 4 and the skilled person understands that 0 indicates the absence of any linear relationship while correlations of −1 to +1 indicate, respectively a perfect negative (inverse) or positive (direct) relationship. Thus, the skilled person can easily determine, based on Tables 2 or 4, which signature genes have comparatively stronger or weaker correlations.

Additionally or alternatively, a ranking based on p-value correlations or other characteristics can be used to determine a sub-combination of the 21 genes for inclusion in a collection of signature genes or for use in a method set forth herein. An exemplary ranking is shown in Table 5. The genes are ranked in Table 5 according to the probability that each is predictive of prostate cancer relapse when evaluated alone or in combination with one or more other genes in the collection of 21 genes. For example, a GEX score based on the expression level of at least one gene in the collection of 21 genes that is predictive of prostate cancer relapse is most likely to include the expression level for the MKI67 gene. Thus, a GEX score based on the expression level of the MKI67 gene alone or in combination with at least one other gene in the collection of 21 genes has the highest probability of correctly predicting prostate cancer relapse. As a further example, a GEX score based on the expression level of at least two genes in the collection of 21 genes that is predictive of prostate cancer relapse is most likely to include the expression level for the MKI67 and GI_2094528 genes. Thus, a GEX score based on the expression level of the MKI67 and GI_2094528 genes exclusively or in combination with at least one other gene in the collection of 21 genes has the highest probability of correctly predicting prostate cancer relapse. Accordingly, collections of signature genes can be built up according to their sequential occurrence in Table 5 (for example, continuing beyond the two collections set forth above, are a set including MKI67, GI_2094528, and HOXC6; a set including MKI67, GI_2094528, HOXC6 and CCK; and so forth).

However, as described in further detail below, a GEX score determined from the expression level of any individual gene in Table 5 or any combination of 2 to 21 genes in Table 5 can be used to predict relapse of prostate cancer so long as the gene expression pattern for the particular gene or combination of genes is correlated with Gleason score. Thus, although the best combination of gene expression levels to include in a 7 gene GEX score for prediction of prostate cancer relapse is derived from the MKI67, GI_2094528, HOXC6, CCK, memD, FBP1, and CDC6 genes, a GEX score including gene expression levels for a variety of other 7 gene combinations are also predictive.

Thus, the invention provides a method of predicting prostate cancer relapse based on the expression patterns for any subset of the 21 genes set forth in Table 5 including, for example, at least 1, 2, 3, 4, 5, 6, 7, 8, 9, 10, 11, 12, 13, 14, 15, 16, 17, 18, 19, or 20 of the 21 genes. The invention also provides a method of predicting prostate cancer relapse based on the expression patterns for any subset of the set of genes consisting of MKI67, GI_2094528, HOXC6, CCK, memD, FBP1, and CDC6 including, for example, at least 1, 2, 3, 4, 5 or 6 of the 7 genes. Similarly, the invention provides a collection of isolated prostate cancer signature genes comprising any subset of the set of genes consisting of MKI67, GI_2094528, HOXC6, CCK, memD, FBP1, and CDC6 including, for example, at least 1, 2, 3, 4, 5 or 6 of the 7 genes.

The sensitivity and specificity of the molecular signature derived from the sets of signature genes provided by the invention provides specific and substantial utility for patients undergoing prostate biopsy for diagnosis of prostate carcinoma based on applicability of the methods described herein to diagnosis as well as prognosis through biopsy samples. Furthermore, the present invention enables the development of a diagnostic test that is technically simple and applicable for routine clinical use, and incorporation into existing prostate cancer nomograms (Group TTABPW, *Nat Rev Genet* 5:229-37 (2004); Ramaswamy, *N Engl J Med* 350:1814-6 (2004); Sullivan Pepe et al. *J Natl Cancer Inst* 93:1054-61 (2001)). Particularly useful, molecular signatures or reference models derived from signatures such as expression patterns are those that are at least as predictive of prostate cancer relapse as Gleason score in prostate cancer patients.

As described herein, archived tissue samples, in particular, formalin-fixed paraffin embedded tissue (FFPE) samples, are particularly useful for establishing a model for relapse prediction because they are generally supported by sufficient clinical follow-up data to allow retrospective studies that correlate gene expression with clinical outcome. By "archived tissue sample" herein is meant tissue samples that have been obtained from a source and preserved. Preferred methods of preservation include, but are not limited to paraffin embedding, ethanol fixation and formalin (including formaldehyde and other derivatives) fixation as are known in the art. The sample may be temporally "old", e.g. months or years old, or recently fixed. For example, post-surgical procedures generally include a fixation step on excised tissue for histological analysis. There are numerous tissue banks and collections comprising exhaustive samples from all stages of a wide variety of disease states, including cancer. Recently developed methods disclosed in U.S. patent application Ser. No. 10/678,608, which is incorporated herein by reference in its entirety, have made it feasible to obtain robust and reproducible gene expression patterns from archived tissues, including formalin-fixed, paraffin-embedded (FFPE) tissues. This ability to access reliable information from archived tissues enabled the discovery that is, in part, the present invention.

In a further embodiment, the invention provides a method for deriving a prostate cancer gene expression score for an individual prostate carcinoma tissue sample by (a) selecting a set of signature genes having an expression pattern that correlates with Gleason scores in prostate cancer patients; (b) independently deriving a prediction score for each of a set of signature genes known to have an expression pattern that correlates with Gleason score in prostate cancer patients, wherein the prediction score correlates gene expression of each individual signature gene with Gleason score; and (c) deriving a prostate cancer gene expression score by calculating the average of said independently derived prediction scores, wherein said prostate cancer gene expression score correlates gene expression of said set of signature genes with Gleason score.

An exemplary gene expression score and method for determining the score are provided in Example I. The gene expression score of Example 1 is calculated from independently derived prediction scores by averaging. In particular embodiments, a gene expression score can be calculated from the independently derived prediction scores with different weights, rather than averaging. It will be understood that any score that is capable of correlating gene expression of individual signature genes with Gleason score can be used in the invention.

In a related yet distinct embodiment, the invention provides a method for predicting the probability of relapse of prostate cancer in an individual by performing the following steps: (a) selecting a set of signature genes having an expression pattern that correlates with Gleason scores in prostate cancer patients; (b) independently deriving a prediction score for each signature gene, wherein the prediction score correlates gene expression of each individual signature gene with Gleason score; (c) deriving a prostate cancer gene expression score by calculating the average of the independently derived prediction scores, wherein the prostate cancer gene expression score correlates gene expression of the set of signature genes with Gleason score (d) comparing the cancer gene expression score to a model to determine the probability of relapse.

The invention further provides a method for predicting the probability of cancer relapse in an individual by performing the following steps: (a) providing a gene expression score derived from independently determined expression levels for a plurality of signature genes in suspected prostate cancer tissue obtained from the individual; (b) providing a model derived from the gene expression scores for a plurality of other individuals and the relapse rates for the plurality of other individuals and (c) comparing the gene expression score to the model to determine the probability of relapse.

In a particular embodiment, the invention provides a method for predicting the probability of relapse of prostate cancer in an individual by performing the steps of (a) providing expression levels for a collection of signature genes from a test individual; (b) deriving a score that captures the expression levels for the collection of signature genes; (c) providing a model comprising information correlating the score with prostate cancer relapse; and (d) comparing the score to the reference model, thereby determining the probability of prostate cancer relapse for the individual.

In a further embodiment, the invention provides a method for predicting the probability of relapse of prostate cancer in an individual by performing the steps of (a) providing expression levels for a collection of signature genes from a test individual, wherein the collection of signature genes comprises at least two genes selected from the group consisting of GI_2094528, KIP2, NRG1, NBL1, Prostein, CCNE2, CDC6; FBP1, HOXC6, MKI67, MYBL2, PTTG1, RAMP, UBE2C, Wnt5A, MEMD, AZGP1, CCK, MLCK, PPAP2B, and PROK1; (b) deriving a score that captures the expression levels for the collection of signature genes; (c) providing a model comprising information correlating the score with prostate cancer relapse; and (d) comparing the score to the reference model, thereby determining the probability of prostate cancer relapse for the individual.

While the present invention is disclosed and exemplified with the 21 signature genes set forth above and further in the context of correlation to Gleason score in prostate cancer, the methods are universally applicable to the diagnosis and prognosis of a broad range of cancers and other conditions. The skilled person apprised of the invention disclosed herein will appreciate that any known predictor of disease extent for any condition can be selected to establish a GEX score for prognosis of relapse that can be more accurate or sensitive than relapse prediction solely based on the known predictor alone.

Accordingly, the invention provides a method for preparing a model for prognosis of an individual having a disease or condition. The method can include the steps of (a) obtaining from different individuals a plurality of tissue samples suspected of having a disease or condition, wherein the clinical outcome corresponding to each of the tissue samples is known, wherein a prognostic score of the tissue samples is known wherein the prognostic score includes stratified grades corresponding to the clinical outcome; (b) selecting a set of signature genes having an expression pattern that correlates positively or negatively in a statistically significant manner with the prognostic score; (c) independently deriving a prediction score for each signature gene in the plurality of tissue samples, wherein the prediction score correlates gene expression of each individual signature gene with the prognostic score; (d) deriving a gene expression (GEX) score based on a combination of the independently derived prediction scores in the plurality of tissue samples, wherein the GEX score correlates gene expression of the set of signature genes with the prognostic score; and (f) correlating the GEX score with the clinical outcome for each of the tissue samples, thereby establishing a model for prognosis of an individual having the disease or condition, wherein the model provides a higher resolution correlation with the clinical outcome than the strata of the prognostic score.

Individuals suspected of having any of a variety of diseases or conditions, such as cancer, can be evaluated using a method of the invention. Exemplary cancers that can be evaluated using a method of the invention include, but are not limited to hematoporetic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myclogenous leukemia (AML), Precursor T lymphoblastic leukemia/lymphoma (ALL), Myclodysplastic syndromes, Chronic Mycloproliferative disorders, Chronic lymphocytic leukemia/small lymphocytic lymphoma (SLL), Chronic Myclogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intaepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embyonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, Insitu Carcinoma, Malignant Lymphoma, Invasive Carcinoma, Chondrosacrcoma, Mesenchymal Chondrosarcoma, cancer of the endocrine system, Osteosarcoma, Adenoma, Ewing Tumor, endocrine Carcinoma, Malignant Giant Cell Tumor, Meningnoma, Adamantinoma, Cramiopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoms, Pineoblastoma, Leiomyosarcoma, Pineocytoma, Angiosarcoma, skin cancer, cancer of the nervous system, Melanoma, Schwannoma, Squamous cell carcinoma, Neurofibroma, Basal cell carcinoma, Malignant Periferal Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

A prognostic score that can be used in the invention includes for example the Gleason score having stratified grades 1-9 that correspond to clinical outcome as set forth elsewhere herein. A further example of a prognostic score that is useful in the invention is cancer staging having stratified grades of stages 1, 2, 3 and 4. The invention can be used to provide a higher resolution correlation with the clinical outcome than the strata of the Gleason or cancer staging prognostic scores. Diseases or conditions other than cancer for which stratified grades have been correlated with clinical outcome can also be used in a method of the invention to determine a prognostic model or to determine a prognosis for an individual suspected of having the disease or condition. Exemplary clinical outcomes that can be determined from a model of the invention include, for example, relapse probability, survival rate, or time to relapse. Another clinical outcome that can be determined from a model of the invention is response to a particular course of therapy such as surgical removal of a tumor, radiation, or chemotherapy.

Any signature gene or combination of signature genes listed within Table 2 or Table 4 can be used in the methods, compositions, and kits of the present invention. Similarly, any additional gene known or discovered to be differentially expressed and correlated with Gleason score can be used in combination with some or all of the signature genes set forth within Table 2 or Table 4 and used in the methods, compositions, and kits of the present invention. In general, it is preferable to use signature genes for which the difference between the level of expression of the signature gene in prostate cancer cells or prostate-associated body fluids and the level of expression of the same signature gene in normal prostate cells or prostate-associated body fluids is as great as possible. Although the difference can be as small as the limit of detection of the method for assessing expression of the signature gene, it is preferred that the difference be at least greater than the standard error of the assessment method, and preferably a difference of at least 1.1-, 1.2-, 1.3-, 1.4-, 1.5-, 1.6-, 1.7-, 1.8-, 1.9-, 2-, 3-, 4-, 5-, 6-, 7-, 8-, 9-, 10-, 15-, 20-, 25-, 100-, 500-, 1000-fold or greater. It also is preferable to use signature genes for which the correlation with Gleason score is more rather than less significant.

The skilled person will appreciate that patient tissue samples containing prostate cells or prostate cancer cells may be used in the methods of the present invention including, but not limited to those aimed at predicting relapse probability. In these embodiments, the level of expression of the signature gene can be assessed by assessing the amount, e.g. absolute amount or concentration, of a signature gene product, e.g., protein and RNA transcript encoded by the signature gene and fragments of the protein and RNA transcript) in a sample, e.g., stool and/or blood obtained from a patient. The sample can, of course, be subjected to a variety of well-known post-collection preparative and storage techniques (e.g. fixation, storage, freezing, lysis, homogenization, DNA or RNA extraction, ultrafiltration, concentration, evaporation, centrifugation, etc.) prior to assessing the amount of the signature gene product in the sample.

In the methods of the invention aimed at preparing a model for prostate cancer relapse prediction, it is understood that the particular clinical outcome associated with each sample contributing to the model must be known. Consequently, the model can be established using archived tissues. In the methods of the invention aimed at preparing a model for prostate cancer relapse prediction, total RNA is generally extracted from the source material of interest, generally an archived tissue such as a formalin-fixed, paraffin-embedded tissue, and subsequently purified. Methods for obtaining robust and reproducible gene expression patterns from archived tissues, including formalin-fixed, paraffin-embedded (FFPE) tissues are taught in United States Patent Publication 2004/0259105, which is incorporated herein by reference in its entirety. Commercial kits and protocols for RNA extraction from FFPE tissues are available including, for example, ROCHE High Pure RNA Paraffin Kit (Roche) MasterPure™ Complete DNA and RNA Purification Kit (EPICENTRE®Madison, Wis.); Paraffin Block RNA Isolation Kit (Ambion, Inc.) and RNeasy™ Mini kit (Qiagen, Chatsworth, Calif.).

The use of FFPE tissues as a source of RNA for RT-PCR has been described previously (Stanta et al., *Biotechniques* 11:304-308 (1991); Stanta et al., *Methods Mol. Biol.* 86:23-26 (1998); Jackson et al., *Lancet* 1:1391 (1989); Jackson et al., *J. Clin. Pathol.* 43:499-504 (1999); Finke et al., *Biotechniques* 14:448-453 (1993); Goldsworthy et al., Mol. Carcinog. 25:86-91 (1999); Stanta and Bonin, *Biotechniques*

24:271-276 (1998); Godfrey et al., *J. Mol. Diagnostics* 2:84 (2000); Specht et al., *J. Mol. Med.* 78:B27 (2000); Specht et al., *Am. J. Pathol.* 158:419-429 (2001)). For quick analysis of the RNA quality, RT-PCR can be performed utilizing a pair of primers targeting a short fragment in a highly expressed gene, for example, actin, ubiquitin, gapdh or other well-described commonly used housekeeping gene. If the cDNA synthesized from the RNA sample can be amplified using this pair of primers, then the sample is suitable for the a quantitative measurements of RNA target sequences by any method preferred, for example, the DASL assay, which requires only a short cDNA fragment for the annealing of query oligonucleotides.

There are numerous tissue banks and collections including exhaustive samples from all stages of a wide variety of disease states, most notably cancer. The ability to perform genotyping and/or gene expression analysis, including both qualitative and quantitative analysis on these samples enables the application of this methodology to the methods of the invention. In particular, the ability to establish a correlation of gene expression and a known predictor of disease extent and/or outcome by probing the genetic state of tissue samples for which clinical outcome is already known, allows for the establishment of a correlation between a particular molecular signature and the known predictor, such as a Gleason score, to derive a GEX score that allows for a more sensitive prognosis than that based on the known predictor alone. The skilled person will appreciate that by building databases of molecular signatures from tissue samples of known outcomes, many such correlations can be established, thus allowing both diagnosis and prognosis of any condition.

Tissue samples useful for preparing a model for prostate cancer relapse prediction include, for example, paraffin and polymer embedded samples, ethanol embedded samples and/or formalin and formaldehyde embedded tissues, although any suitable sample may be used. In general, nucleic acids isolated from archived samples can be highly degraded and the quality of nucleic preparation can depend on several factors, including the sample shelf life, fixation technique and isolation method. However, using the methodologies taught in United States Patent Publication 2004/0259105, which have the significant advantage that short or degraded targets can be used for analysis as long as the sequence is long enough to hybridize with the oligonucleotide probes, highly reproducible results can be obtained that closely mimic results found in fresh samples.

Archived tissue samples, which can be used for all methods of the invention, typically have been obtained from a source and preserved. Preferred methods of preservation include, but are not limited to paraffin embedding, ethanol fixation and formalin, including formaldehyde and other derivatives, fixation as are known in the art. A tissue sample may be temporally "old", e.g. months or years old, or recently fixed. For example, post-surgical procedures generally include a fixation step on excised tissue for histological analysis. In a preferred embodiment, the tissue sample is a diseased tissue sample, particularly a prostate cancer tissue, including primary and secondary tumor tissues as well as lymph node tissue and metastatic tissue.

Thus, an archived sample can be heterogeneous and encompass more than one cell or tissue type, for example, tumor and non-tumor tissue. Preferred tissue samples include solid tumor samples including, but not limited to, tumors of the prostate. It is understood that in applications of the present invention to conditions other than prostate cancer the tumor source can be brain, bone, heart, breast, ovaries, prostate, uterus, spleen, pancreas, liver, kidneys, bladder, stomach and muscle. Similarly, depending on the condition, suitable tissue samples include, but are not limited to, bodily fluids (including, but not limited to, blood, urine, serum, lymph, saliva, anal and vaginal secretions, perspiration and semen, of virtually any organism, with mammalian samples being preferred and human samples being particularly preferred). In embodiments directed to methods of establishing a model for relapse prediction, the tissue sample is one for which patient history and outcome is known. Generally, the invention methods can be practiced with the signature gene sequence contained in an archived sample or can be practiced with signature gene sequences that have been physically separated from the sample prior to performing a method of the invention.

If required, a nucleic acid sample having the signature gene sequence(s) are prepared using known techniques. For example, the sample can be treated to lyse the cells, using known lysis buffers, sonication, electroporation, etc., with purification and amplification as outlined below occurring as needed, as will be appreciated by those in the art. In addition, the reactions can be accomplished in a variety of ways, as will be appreciated by those in the art. Components of the reaction may be added simultaneously, or sequentially, in any order, with preferred embodiments outlined below. In addition, the reaction can include a variety of other reagents which can be useful in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., can be used, depending on the sample preparation methods and purity.

In a preferred embodiment mRNA is isolated from paraffin embedded samples as is known in the art. Preferred methods include the use of the Paraffin Block RNA Isolation Kit by Ambion (Catalog number 1902, which instruction manual is incorporated herein by reference) or the high pure RNA paraffin kit by Roche (cat #3270289). Samples of mRNA can be obtained from other samples using methods known in the art including for example, those described in Sambrook et al., *Molecular Cloning: A Laboratory Manual,* 3rd edition, Cold Spring Harbor Laboratory, New York (2001) or in Ausubel et al., *Current Protocols in Molecular Biology*, John Wiley and Sons, Baltimore, Md. (1998), or those that are commercially available such as the Invitrogen PureLink miRNA isolation kit (cat# K1570) or mRNA isolation kits from Ambion (Austin, Tex.). Once prepared, mRNA or other nucleic acids are analyzed by methods known to those of skill in the art. The nucleic acid sequence corresponding to a signature gene can be any length, with the understanding that longer sequences are more specific. Recently developed methods for obtaining robust and reproducible gene expression patterns from archived tissues, including formalin-fixed, paraffin-embedded (FFPE) tissues as taught in United States Patent Application Publication No. 2004/0259105 have the significant advantage that short or degraded targets can be used for analysis as long as the sequence is long enough to hybridize with the oligonucleotide probes. Thus, even degraded target nucleic acids can be analyzed. Preferably a nucleic acid corresponding to a signature gene is at least 20 nucleotides in length. Preferred ranges are from 20 to 100 nucleotides in length, with from 30 to 60 nucleotides being more preferred and from 40 to 50 being most preferred.

In addition, when nucleic acids are to be detected preferred methods utilize cutting or shearing techniques to cut the nucleic acid sample containing the target sequence into a size that will facilitate handling and hybridization to the target.

This can be accomplished by shearing the nucleic acid through mechanical forces (e.g. sonication) or by cleaving the nucleic acid using restriction endonucleases, or any other methods known in the art. However, in most cases, the natural degradation that occurs during archiving results in "short" oligonucleotides. In general, the methods of the invention can be done on oligonucleotides as short as 20-100 basepairs, with from 20 to 50 being preferred, and between 40 and 50, including 44, 45, 46, 47, 48 and 49 being the most preferred.

Tissue samples useful in a method of the invention for deriving a prostate cancer gene expression score or in a method of the invention for predicting the probability of relapse of prostate cancer in an individual, include the tissue samples described above as useful for preparing a model for prostate cancer relapse prediction, but also include fresh and non-archived samples. Unlike for tissue samples useful for preparing a model for prostate cancer relapse prediction, the tissues used for deriving a prostate cancer GEX score or in a method of the invention for predicting the probability of relapse of prostate cancer in an individual, for obvious reasons, do not have the requirement that clinical outcome be known. Consequently, freshly obtained tissue samples can also be used in the individual methods for GEX score determination and relapse prediction methods, such as in a prospective study or clinical trial.

The methods of the invention depend on the detection of differentially expressed genes for expression profiling across heterogeneous tissues. Thus, the methods depend on profiling genes whose expression in certain tissues is activated to a higher or lower level in an individual afflicted with a condition, for example, cancer, such as prostate cancer, relative to its expression in a non-cancerous tissues or in a control subject. Gene expression can be activated to a higher or lower level at different stages of the same conditions and a differentially expressed gene can be either activated or inhibited at the nucleic acid level or protein level, or may be subject to alternative splicing to result in a different polypeptide product. Such differences can be evidenced by a change in mRNA levels, surface expression, secretion or other partitioning of a polypeptide, for example. For the purpose of this invention, differential gene expression is considered to be present when there is at least about 1.1-fold, 1.2-fold, 1.3-fold, 1.4-fold, 1.5-fold, 1.6-fold, 1.7-fold, 1.8-fold, 1.9-fold, to two-fold, preferably at least about four-fold, more preferably at least about six-fold, most preferably at least about ten-fold difference between the expression of a given gene in normal and diseased tissues.

Differential signature gene expression can be identified, or confirmed using methods known in the art such as quantitative RT-PCR. In particular embodiments, differential signature gene expression can be identified, or confirmed using microarray techniques. Thus, the signature genes can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. In a preferred embodiment the technology combines fiber optic bundles and beads that self-assemble into an array. Each fiber optic bundle contains thousands to millions of individual fibers depending on the diameter of the bundle. Sensors are affixed to each bead in a given batch. The particular molecules on a bead define that bead's function as a sensor. To form an array, fiber optic bundles are dipped into pools of coated beads. The coated beads are drawn into the wells, one bead per well, on the end of each fiber in the bundle. The present invention is not limited to the solid supports described above. Indeed, a variety of other solid supports are contemplated including, but not limited to, glass microscope slides, glass wafers, gold, silicon, microchips, and other plastic, metal, ceramic, or biological surfaces. Microarray analysis can be performed by commercially available equipment, following manufacturer's protocols, such as by using Illumina's technology.

Exemplary arrays that are useful include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No. WO 00/63437, each of which is hereby incorporated by reference. Other arrays having particles on a surface include those set forth in US 2005/0227252; US 2006/0023310; US 2006/006327; US 2006/0071075; US 2006/0119913; U.S. Pat. No. 6,489,606; U.S. Pat. No. 7,106,513; U.S. Pat. No. 7,126,755; U.S. Pat. No. 7,164,533; WO 05/033681; and WO 04/024328, each of which is hereby incorporated by reference.

An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Further examples of commercially available microarrays that can be used in the invention include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference.

A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies. Other microarrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

DASL can be used for quantitative measurements of RNA target sequences as well as for DNA target sequences. DASL is described, for example, in Fan et al., *Genome Res.* 14:878-85 (2004); US 2003/0108900 and US 2004/0259105, each of which is incorporated herein by reference. Notably, the sensitivity of DASL using RNA from paraffin samples is about 80% compared to the assay using RNA prepared from fresh frozen samples, with results up to 90% sensitivity observed. Gene expression can be monitored and compared in formalin-fixed, paraffin-embedded clinical samples archived for more than 5 years.

The expression patterns for signature genes are determined based on quantitative detection of nucleic acids or oligonucleotides corresponding to the signature genes, which means at least two nucleotides covalently linked together. Thus, the invention also provides a collection of nucleic acids and oligonucleotides that correspond to a signature gene or a set of signature genes. A nucleic acid useful in the methods of the invention will generally contain phosphodiester bonds, although in some cases, nucleic acid analogs are included that may have alternate backbones, including, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, *C & E News Jun.* 2, 1997 page 35. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs.

The nucleic acids corresponding to signature genes can be single stranded or double stranded, as specified, or contain portions of both double stranded or single stranded sequence. The nucleic acid can be DNA, both genomic and cDNA, RNA or a hybrid, where the nucleic acid contains any combination of deoxyribo- and ribo-nucleotides, and any combination of bases, including, for example, uracil, adenine, thymine, cytosine, guanine, inosine, xanthine hypoxanthine, isocytosine, isoguanine. A nucleic acid sequence corresponding to a signature gene can be a portion of the gene, a regulatory sequence, genomic DNA, cDNA, RNA including mRNA and rRNA, or others.

A nucleic acid sequence corresponding to a signature gene can be derived from the tissue sample, or from a secondary source such as a product of a reaction such as, for example, a detection sequence from an invasive cleavage reaction, a ligated probe from an OLA or DASL reaction, an extended probe from a PCR reaction, or PCR amplification product, ("amplicon"). Exemplary methods for preparing secondary probes from target sequences are described in US 2003/0108900; US 2003/0170684; US 2003/0215821; US 2004/0121364; and US 2005/0181394. Thus, a nucleic acid sequence corresponding to a signature gene can be derived from the primary or from a secondary source of nucleic acid.

As will be appreciated by those in the art, a complementary nucleic acid sequence useful in the methods of the invention can take many forms and probes are made to hybridize to nucleic acid sequences to determine the presence or absence of the signature gene in a sample. In a preferred embodiment, a plurality of nucleic acid sequences is detected. As used herein, "plurality" or grammatical equivalents herein refers to at least 2, 10, 20, 25, 50, 100 or 200 different nucleic sequences, while at least 500 different nucleic sequences is preferred. More preferred is at least 1000, with more than 5000 or 10,000 particularly preferred and more than 50,000 or 100,000 most preferred. Detection can be performed on a variety of platforms such as those set forth above or in the Examples.

The expression level of a signature gene in a tissue sample can be determined by contacting nucleic acid molecules derived from the tissue sample with a set of probes under conditions where perfectly complementary probes form a hybridization complex with the nucleic acid sequences corresponding to the signature genes, each of the probes including at least two universal priming sites and a signature gene target-specific sequence; amplifying the probes forming the hybridization complexes to produce amplicons; and detecting the amplicons, wherein the detection of the amplicons indicates the presence of the nucleic acid sequences corresponding to the signature gene in the tissue sample; and determining the expression level of the signature gene.

In the context of the present invention, multiplexing refers to the detection, analysis or amplification of a plurality of nucleic acid sequences corresponding to the signature genes. In one embodiment multiplex refers to the number of nucleic acid sequences corresponding to a signature gene to be analyzed in a single reaction, vessel or step. The multiplexing method is useful for detection of a single nucleic acid sequence corresponding to a signature gene as well as a plurality of nucleic acid sequences corresponding to a set of signature genes. In addition, as described below, the methods of the invention can be performed simultaneously and in parallel in a large number of tissue samples.

The expression level of nucleic acid sequences corresponding to a set of signature genes in a tissue sample can be determined by contacting nucleic acid molecules derived from the tissue sample with a set of probes under conditions where complementary probes form a hybridization complex with the signature gene-specific nucleic acid sequences, each of the probes including at least two universal priming sites and a signature gene-specific nucleic acid sequence; amplifying the probes forming the hybridization complexes to produce amplicons; detecting the amplicons, wherein the detection of the amplicons indicates the presence of the nucleic acid sequences corresponding to the set of signature genes in the tissue sample; and determining the expression level of the target sequences, wherein the expression of at least two, at least three, at least five signature gene-specific sequences is detected.

The presence of one, two or a plurality of nucleic acid sequences corresponding to a set of signature genes can be determined in a tissue sample using single, double or multiple probe configurations. The methods of the invention can be practiced with tissue samples having substantially degraded nucleic acids. Although methods for pre-qualifying samples with respect to nucleic acid degradation are described above, those skilled in the art will recognize that other detection methods described herein or known in the art can be used to detect RNA levels in a sample suspected of having degraded nucleic acids, thereby determine the level of nucleic acid degradation in accordance with the invention.

The present invention particularly draws on methodologies outlined in US 2003/0215821; US 2004/0018491; US 2003/0036064; US 2003/0211489, each of which is expressly incorporated by reference in their entirety. In addition, universal priming methods are described in detail in US 2002/0006617; US 2002/0132241, each of which is expressly incorporated herein by reference. In addition, multiplex methods are described in detail US 2003/0211489; US 2003/0108900, each of which is expressly incorporated herein by reference. In general, the methods of the invention can be performed in a variety of ways, as further described below and in the cited applications incorporated by reference. For example, mRNA signature samples can initially be subjected to a "complexity reduction" step, whereby the presence of a particular target is confirmed by adding probes that are enzymatically modified in the presence of the signature gene-specific nucleic acid sequence. The modified probes are then amplified and detected in a wide variety of ways. Preferred embodiments draw on multiplexing methods, which allow for the simultaneous detection of a number of nucleic acid sequences, for example, corresponding to a set of signature genes, as well as multiplexing amplification reactions, for example by using universal priming sequences to do multiplex PCR reactions. If desired, the initial step also can be both a complexity reduction and an amplification step.

"Nucleic acid sequence" or grammatical equivalents herein referred to as corresponding to a signature gene means the order and type of nucleotides in a single strand of nucleic acid. The nucleic sequence can be a portion of a gene, a regulatory sequence, genomic DNA, cDNA, RNA including mRNA and rRNA, or others. A preferred embodiment utilizes mRNA as the primary target sequence. As is outlined herein, the nucleic acid sequence can be a sequence from a sample, or a secondary target such as, for example, a product of a reaction such as a detection sequence from an invasive cleavage reaction, a ligated probe from an OLA or DASL reaction, an extended probe from a PCR reaction, or PCR amplification product, ("amplicon"). A nucleic acid sequence corresponding to a signature gene can be any length, with the understanding that longer sequences are more specific. Probes are made to hybridize to nucleic acid sequences to determine the presence or absence of expression of a signature gene in a sample.

The invention also provides a collection of isolated probes specific for prostate cancer signature genes consisting essentially of probes specific for GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated probes specific for prostate cancer signature genes consisting of probes specific for GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. The invention also provides a collection of isolated probes specific for prostate cancer signature genes comprising probes specific for GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. Also provided is a collection of isolated probes specific for prostate cancer signature genes comprising probes specific for a subset of the collection consisting of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B and PROK1. Exemplary subsets include those set forth elsewhere herein.

Thus, the invention also provides a collection of isolated probes specific for prostate cancer signature genes including any subset of the 21 genes set forth in Table 5 including, for example, at least 1, 2, 3, 4, 5, 6, 7, 8, 9, 10, 11, 12, 13, 14, 15, 16, 17, 18, 19, or 20 of the 21 genes. The invention also provides a collection of isolated probes specific for prostate cancer signature genes including any subset of the set of genes consisting of MKI67, GI_2094528, HOXC6, CCK, memD, FBP1, and CDC6 including, for example, at least 2, 3, 4, 5 or 6 of the 7 genes.

A method of the invention can further include a step of producing a report identifying, for example, a reference model, a set of signature genes, a prediction score, a GEX score. The report can include data obtained from a method of the invention in a format that can be subsequently analyzed to identify a reference model, a set of signature genes, a prediction score, a GEX score. Thus, the invention further provides a report of at least one result obtained by a method of the invention. A report of the invention can be in any of a variety of recognizable formats including, for example, an electronic transmission, computer readable memory, an output to a computer graphical user interface, compact disk, magnetic disk or paper. Other formats suitable for communication between humans, machines or both can be used for a report of the invention. The methods of the invention can, in part, be conveniently performed on a computer apparatus. Performing one or more steps of an invention method on a computer apparatus is particularly useful when analyzing a large number of parameters such as a large number of tissue samples.

In one embodiment, the invention provides a diagnostic method of assessing whether a patient who has had prostate cancer has a higher than normal risk for recurrence of the prostate cancer or other cancer, including the steps of comparing the GEX score calculated by a method of the invention in a patient sample comparing it to a model for relapse prediction prepared by a method of the invention. A similar GEX score in the patient sample as compared to the model provides a more accurate relapse predictor than Gleason score alone.

In one embodiment, the invention provides a diagnostic method of assessing whether a patient has a higher than normal risk of having or developing a prostate cancer. Small samples, such as those obtained using LCM in needle biopsies, with or without tumor glands, can be used to assess outcomes prior to definitive therapy. This test can give information on diagnosis as well as prognosis through needle biopsy samples. Such a test provides a diagnostic test for routine clinical use.

The invention includes compositions, kits, and methods for assessing the probability of relapse of cancer for an individual from which a sample is obtained. The sample can be, for example, an archived tissue sample or a sample obtained from a patient. Where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of gene expression in the sample. Such methods are well known in the art and within the skill of the ordinary artisan. A kit is any manufacture (e.g. a package or container) including at least one reagent, e.g. a probe, for specifically detecting the expression of a signature gene of the invention. The kit may be promoted, distributed, or sold as a unit for performing the methods of the present invention. It is recognized that the compositions, kits, and methods of the invention will be of particular utility to patients having a history of prostate cancer and their medical advisors.

The practice of the present invention employs, unless otherwise indicated, conventional techniques of molecular biology (including recombinant techniques), microbiology, cell biology, and biochemistry, which are within the skill of the art. Such techniques are explained in the literature, such as, "Molecular Cloning: A Laboratory Manual", Second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", Fourth edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Although the use of the 21 genes, and subsets thereof, has been exemplified with respect to prognosis and diagnosis methods utilizing expression levels of mRNA species produced by these genes, it will be understood that similar diagnostic and prognostic methods can utilize other measures such as methylation levels for the genes which can be correlated with expression levels or a measure of the level or activities of the protein products of the genes. Methylation can be determined using methods known in the art such as those set forth in U.S. Pat. No. 6,200,756 or US 2003/0170684, each of which is incorporated herein by reference. The level and activity of proteins can be determined using methods known in the art such as antibody detection techniques or enzymatic assays particular to the activity being evaluated. Furthermore, prognosis or diagnosis can be based on the presence of mutations or polymorphisms identified in the genes that affect expression of the gene or activity of the protein product.

It is understood that modifications which do not substantially affect the activity of the various embodiments of this invention are also included within the definition of the invention provided herein. Accordingly, the following examples are intended to illustrate but not limit the present invention.

Example I

Correlation Between Gene Expression Signature and Gleason Score

This example shows the calculation of a Gene EXpression score (GEX), which is an expression analogy of Gleason score derived from 16 genes and which showed a better correlation (r=0.62) with Gleason score than correlation of any individual gene.

A candidate gene approach focused on a set of "informative" genes that are the most relevant to the subjects of this study was taken as has been described by (Lossos et al., N Engl J Med 350:1828-37 (2004); Paik et al., 2004; Ramaswamy et al., J Clin Oncol 20:1932-41, (2002); van de Vijver et al., N Engl J Med 347:1999-2009 (2002)). The genes were selected based on: (1) Biological relevance. These include tumor suppressor genes and oncogenes, genes that are indirectly involved in cancer development, for example, DNA repair genes; metastasis-inhibitor genes, genes regulated by various signaling pathways, and/or responsible for altered cell growth and differentiation, apoptosis; or genes considered to be targets for oncogenic transformation. (2) Publicly reported lists of genes differentially expressed in prostate cancer as described by (Bettuzzi et al., Cancer Res 63:3469-72 (2003); Dhanasekaran et al., Nature 412:822-6 (2001); Ernst et al. Am J Pathol 160:2169-80 (2002); Febbo and Sellers, J Urol 170:S11-9; discussion S19-20 (2003); Glinsky et al., J Clin Invest 113:913-23 (2004); Henshall et al., Cancer Res 63:4196-203 (2003); Lapointe et al., Proc Natl Acad Sci USA 101:811-6 (2004); Latil et al., Clin Cancer Res 9:5477-85 (2003); Luo et al., Prostate 51:189-200 (2002); Nelson et al., N Engl J Med 349:366-81 (2003); Ramaswamy et al., Nat Genet 33:49-54 (2003); Singh et al., Cancer Cell 1:203-9 (2002); Stamey et al., J Urol 166:2171-7, (2001); Stuart et al., Proc Natl Acad Sci USA 101:615-20 (2004); van't Veer et al., Nature 415:530-6 (2002); Welsh et al., Cancer Res 61:5974-8 (2001). As set forth in Table 3, a list of 512 genes was selected from these gene lists based on their overlapping occurrences among the studies, differential expression levels and biological relevance. In addition, 20 negative controls were included, designed to target sequences which are not present in the human genome and used to assess assay specificity.

The RNA samples assayed in this study were extracted from FFPE tissues. 200 ng of total RNA isolated from each FFPE tissue block was converted into cDNA, and two independent DASL assays were performed for each RNA sample as described by (Fan et al., Genome Res. 14:878-85 (2004)).

Briefly, surgically removed specimens (radical prostatectomy specimens) were processed under routine pathological protocol, and examined by at least two pathologists. A study number was assigned to the specimen and the patient identification information (names and hospital identification number) was also recorded at the time of specimen retrieval. This data were stored in a Microsoft Excel and Access database. The specimens usually were received in the pathology laboratory fresh within 45 minutes of removal. Each specimen was fixed in 10% buffered formalin overnight.

Representative sections were submitted for tissue processing and paraffin embedding. 5-μm thick sections were made for routine Hamatoxylin and eosin stains. Specific tissue blocks that included areas of carcinoma were selected for RNA extraction. RNA was procured from FFPE cancer tissue and nearby non-cancerous tissue. For each pathologic tissue, the percentage of tumor content was estimated and used as a reference for gene expression pattern analysis. RNA was extracted from four to five 5-μm sections using an RNA extraction kit (Roche High Pure RNA Paraffin kit), yielding 0.5-3 μg of total RNA.

A total of 71 tissue samples were entered into this study (Table 1). This consists of 29 cases of prostate carcinomas of low risk group patients, 26 cases of carcinomas of intermediate risk group, 16 cases of carcinomas of high risk group. Low risk group patients had a serum PSA≦10 ng/ml, Gleason summary score≦6 and a digital rectal examination (DRE) of T1c/T2a. Intermediate risk group patients had a serum PSA 10-20 ng/ml, Gleason summary score of 7 and DRE T2b/T2c. The high risk group patients had a serum PSA>20 ng/ml, Gleason summary score of 8-10 and DRE T3a/T3b. All tumor blocks contained at least 10% of malignant glands. In addition, 34 matched, non-tumor prostate tissues were used as controls. These tissues were various compositions of inflammation, stroma, benign glandular hyperplasia, and glandular atrophy.

Data regarding tissue samples were initially stored in a Microsoft Access file detailing the location, specimen number, and pathologic diagnosis. Approval was obtained from the UCSD IRB (#040487x) to study patient's existing tissue materials and review of pertinent medical records. The clinical information was de-identified from the original patient identification prior to data analysis so the findings will not be possible to trace back to the original patient.

To identify genes that are prognostically significant, patient history was provided for clinical correlation. Review of clinical data included demographic, clinical and laboratory data that is available either at the time of specimen collection (cross-sectional data) or becomes available at a later time point (longitudinal data). Data obtained from the patient treatment file (PTF), outpatient clinic file (OPC), and Computerized Patient Record System (CPRS), including lab, Systematized Nomenclature of Medicine (SNOMED), and tumor registry data. Information included 6-84 months follow up on the study patients and control subjects. Information relevant to the patient's diagnosis were obtained (Table 1), which include, but are not limited to, age, ethnicity, serum PSA at the time of surgery, tumor localization, pertinent past medical history related to co-morbidity, other oncological history, family history for cancer, physical exam findings, radiological findings, biopsy date, biopsy result, types of operation performed (radical retropubic or radical perineal prostatectomy), TNM staging, neoadjuvant therapy (i.e. chemotherapy, hormones), adjuvant or salvage radiotherapy, hormonal therapy for a rising PSA (biochemical disease relapse), local vs. distant disease recurrence and survival outcome.

TABLE 1

| | |
|---|---|
| Mean Age | 68.9 (55-81) |
| Mean PSA | 8.1 (1.76-24.03) |
| Months Follow Up | 43.9 ± 15 (6-84) |

| | Numbers |
|---|---|
| Biopsy Risk Group | |
| Low | 29 |
| Intermediate | 26 |
| High | 16 |
| Gleason Grade Distribution | |
| 5 | 2 |
| 6 | 8 |
| 7 | 31 |
| 8 | 26 |
| 9 | 3 |
| Relapse | |
| No | 55 |
| Yes | 16 |
| Survival | |
| Alive | 60 |
| Dead | 11 |
| AJCC TNM Stage | |
| I | 0 |
| II | 53 |
| III | 15 |
| IV | 3 |

Figure 6:
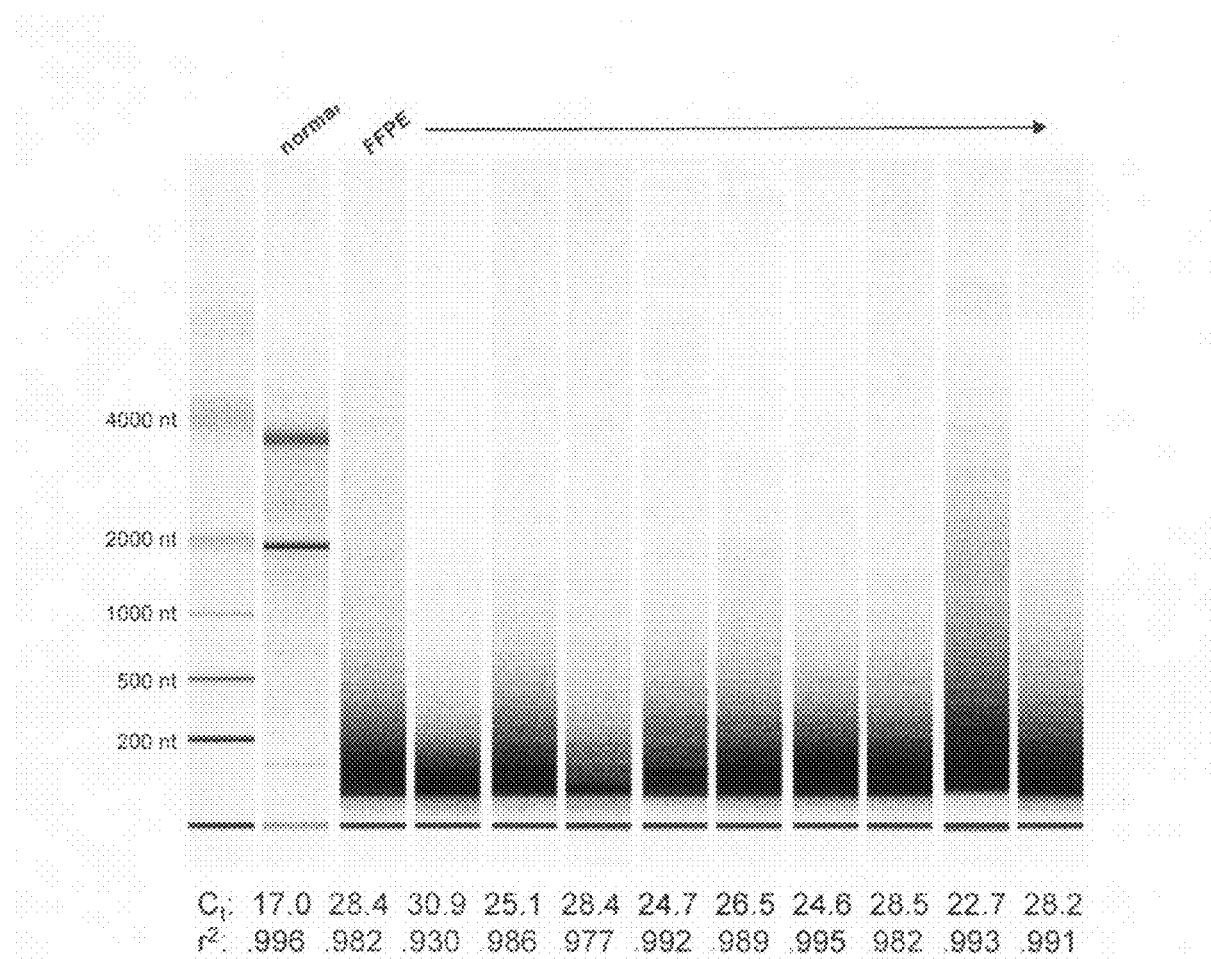
FIG. 6 shows FFPE-derived RNA metrics. Bioanalyzer traces for 10 FFPE-derived prostate cancer RNAs are shown. These traces represent the more marginal FFPEs. Ct was measured for a 90 by amplicon from the RPL13a gene using SYBR Green detection. $R^2$ represents the correlation between replicate DASL assays for the same cDNA run in parallel.

To assess their integrity, the RNA samples were measured on a Bioanalyzer (FIG. 7). In addition, aliquots of the cDNA reactions were taken for a real-time PCR analysis of a highly expressed housekeeping gene (RPL13A). Highly reproducible gene expression profiles were obtained for the replicates of each FFPE sample ($R^2$=0.99), even though a wide range of RNA degradation was detected in these samples that had up to 8 cycle difference in qPCR (i.e. ~170-fold difference in "PCR-able" RNA input) for the RPL13A gene (FIG. 6). Under the conditions used, it was determined that a reasonable expectation of reliable data in the DASL assay was assured if samples did not exhibit a Ct of more than 28 cycles. In addition, similar expression profiles were obtained with RNAs extracted independently from separate cuts of the same paraffin tissue blocks ($R^2$=0.93) (data not shown).

The randomly ordered BeadArray™ technology (Michael et al., *Anal Chem* 70, 1242-8 (1998); Walt, *Science* 287, 451-2 (2000)) has been developed at Illumina as a platform for SNP genotyping (Fan et al., *Cold Spring Harb Symp Quant Biol* 68:69-78 (2003); Gunderson et al., *Nat Genet* 37:549-54 (2005)), gene expression profiling (Bibikova et al. *Am J Pathol* 165:1799-807 (2004); Fan et al., *Genome Res* 14:878-85 (2004); Kuhn et al., *Genome Res* 14:2347-56 (2004); Yeakley et al., *Nat Biotechnol* 20:353-8 (2002)) and DNA methylation detection (Bibikova et al., *Genome Res* 16:383-93 (2006)). Each array was assembled on an optical fiber bundle consisting of about 50,000 individual fibers fused together into a hexagonally packed matrix. The ends of the bundle were polished, and one end was chemically etched to create a microscopic well in each fiber. These wells were each filled with a 3-micron diameter silica bead. Each derivatized bead had several hundred thousand copies of a particular oligonucleotide covalently attached and available for hybridization. Bead libraries were prepared by conjugation of oligonucleotides to silica beads, followed by quantitative pooling together of the individual bead types. Because the beads were positioned randomly on the array, a decoding process was carried out to determine the location and identity of each bead in every array location (Gunderson et al., *Genome Res* 14:870-7 (2004)). Each of the 1,624 bead types in the resulting universal array was present at an average redundancy of about 30. Consequently, each assay measurement was the result of data averaged from multiple beads, which increased precision and greatly reduced the possibility of error.

To further increase sample throughput, the arrays were formatted into a matrix, in a pattern that matched the wells of standard 96-well microtiter plates. The matrix format allows streamlined sample handling. By bringing the array to the sample (literally dipping it into the microtiter well), sample and array processing is simplified and integrated for handling of 96 separate samples simultaneously.

A flexible, sensitive, accurate and cost-effective gene expression profiling assay, the DASL (for DNA-mediated annealing, selection, extension and ligation) assay, was used for parallel analysis of over 1500 sequence targets (e.g. 500 genes at 3 probes per gene) (Fan et al., supra 2004). In this assay, two oligos were designed to target a specific gene sequence. Total RNA was first converted to cDNA by random priming. The corresponding query oligos hybridized to the cDNA, and were extended and ligated enzymatically. The ligated products were then amplified and fluorescently labeled during PCR, and finally detected by binding to address sequences on the universal array. The hybridization intensity was used as a measurement of the original mRNA abundance in the sample.

Unlike most of the other array technologies that use an in vitro transcription (IVT)-mediated sample labeling procedure (Phillips and Eberwine, *Methods* 10, 283-8 (1996)), DASL uses random priming in the cDNA synthesis, and therefore does not depend on an intact poly-A tail for T7-oligo-d(T)·priming. In addition, the assay utilizes a relatively short target sequence of about 50 nucleotides for query oligonucleotide annealing, thus allowing microarray analyses of degraded RNAs (Bibikova et al., *Am J Pathol* 165: 1799-807 (2004); Bibikova et al., *Clin Chem* 50:2384-6 (2004))

Standard software developed at Illumina was used for automatic image registration (Galinsky, *Bioinformatics* 19:1832-6 (2003)) and extraction of feature intensities. Briefly, the feature extraction algorithm represents a weighted 6×6 average of pixel intensities. The outlier algorithm was implemented at the feature level (each probe sequence was represented by 30 features on average) to remove features that fell outside of a robust confidence interval of the median response. Array data was normalized using the "rank invariant" method in Illumina's BeadStudio software, with sample VA_73 being the reference sample.

In the interest of having the tissue samples mimicking clinical situation as much as possible, 71 tumors with various Gleason grades were used. Some tumors have uniformly one grade, while others have a primary and a secondary grade. The tumors with one grade were counted twice to comprise a Gleason Score (GS; i.e. Gleason Grades 3+3=Gleason Score 6). Gleason Scores of two primary tumor patterns were the sum of the two Gleason Grades (i.e. Primary Gleason Grade 4 and secondary Gleason Grade 3 would have a Gleason Score of 7). All 71 tumor samples contained tumor content higher than 10% and inflammation content less than 5%. For each gene, Pearson's correlation coefficient was computed between its expression level and Gleason score. P-values were assigned to observed correlations by a permutation test. Sample labels were randomly permuted 10,000 times and the correlation values were determined. For each gene, the p-value is the fraction of random permutations that resulted in higher correlation value than the one seen with correct sample labels. A cutoff value of 14/10,000 which corresponds to false discovery rate (FDR) adjusted p-value=0.05 was used and a list of 16 genes was obtained. For all the selected genes, a fitted linear model was used (using rlm function with method "MM" in MASS library of the R statistical package) to predict Gleason grades and the average of 16 independently derived prediction scores was used as a gene expression analogy (GEX score) of the Gleason score. Kaplan-Meier analysis was performed using SurvDiff function from SURVIVAL library of R package with parameters corresponding to a log-rank test.

Differential gene expression is present within prostate carcinomas of patients with various degrees of Gleason grade, thus contributing to different clinical outcomes within the groups. The permutation method described above was used to identify genes that were either positively or negatively correlated with Gleason score and generated a panel of 11 positively correlated genes: CCNE2, CDC6, FBP1, HOXC6, MKI67, MYBL2, PTTG1, RAMP, UBE2C, Wnt5A, MEMD; and 5 negatively correlated: AZGP1, CCK, MLCK, PPAP2B, and PROK1. The 16 genes can be classified into several groups based on their biological functions: (1) proliferation: MKI67, MYBL2, Wnt5A, PTTG1, AZGP1, and PROK1; (2) cell cycle: CCNE2 (cyclin E2), CDC6, MKI67, MYBL2, PTTG1, UBE2C; (3) differentiation: HOXC6, Wnt5A; (4) cell adhesion: MEMD, AZGP1, and MLCK; (5) signal transduction: Wnt5A, CCK, MLCK, and UBE2C; (6) basic metabolism: FBP1, AZGP1, PPAP2B, and RAMP (a protease).

TABLE 2

Pearson's correlation coefficient (r) between gene expression and Gleason score, and the p-value calculated from the permutation test.

| GeneID | Correlation | Pval |
| --- | --- | --- |
| AZGP1 | −0.35498 | 2.00E−04 |
| CCK | −0.34259 | 9.00E−04 |
| CCNE2 | 0.364285 | 9.00E−04 |
| CDC6 | 0.372737 | 2.00E−04 |
| FBP1 | 0.337464 | 0.0013 |
| HOXC6 | 0.503815 | 0 |
| MKI67 | 0.392234 | 0 |
| MLCK | −0.34564 | 7.00E−04 |
| MYBL2 | 0.37886 | 0 |
| PPAP2B | −0.35176 | 8.00E−04 |
| PROK1 | −0.36189 | 7.00E−04 |
| PTTG1 | 0.382119 | 4.00E−04 |
| RAMP | 0.448571 | 0 |
| UBE2C | 0.325166 | 0.0011 |
| Wnt5A | 0.394576 | 4.00E−04 |
| memD | 0.351226 | 0.0014 |

Based on the expression profiles of these 16 genes, a Gene EXpression score (GEX, an expression analogy of Gleason score) was calculated. The GEX score had better correlation (r=0.62) with Gleason score than correlation of any individual gene. The GEX score exhibited a nonlinear pattern, in which the expression signature score was flat when GS<7, and then started rising around GS=7 and GS=9 (FIG. 1), pointing to the presence of three distinct molecular stages among the prostate cancer patients [GS5-N, GS6-N, GS6-Y and GS7-N], [GS7-Y, GS8-N and GS8-Y], and GS9-Y, and this may correspond to Gleason pattern grade 3, 4, and 5, respectively. Patients which experienced relapse tended to have higher GEX scores despite having identical Gleason scores (see FIG. 1: GS6-Y vs. GS6-N, GS7-Y vs. GS7-N, and GS8-Y vs. GS8-N).

In order to find out whether the GEX was significantly different in tumor versus non-tumor samples, a total of 126 samples of FFPE cancer (N=79) and non-cancer (N=47) prostate tissues were profiled. "Cancer" sections included 10-90% adenocarcinoma in the block. The mean GEX on the cancer tissues were 7.38+/−0.35 and the GEX on non-cancer prostate tissues were 7.2+/−0.16 (p=0.0013), indicating the GEX scores significantly correlated with the diagnostic tissues of cancer versus benign prostate tissues.

TABLE 3

512 genes selected for this study.

| Gene-Symbol | GenBank ID |
| --- | --- |
| ABCA5 | GI_27262623 |
| ABCF3 | GI_8922935 |
| ACADSB | GI_38373685 |
| ACPP | GI_6382063 |
| ADAMTS1 | GI_11038653 |
| ADD2 | GI_9257191 |
| ADPRT | GI_11496989 |
| AKAP2 | GI_22325354 |
| AKR1C3 | GI_24497582 |
| ALDH1A2 | GI_25777723 |
| ALDH4A1 | GI_25777733 |
| ALG-2 | GI_22027539 |
| ALOX15B | GI_4557308 |
| AMACR | GI_31541879 |
| AML1 | GI_19923197 |
| ANGPT2 | GI_4557314 |
| ANGPTL2 | GI_34577067 |
| ANPEP | GI_4502094 |

TABLE 3-continued

512 genes selected for this study.

| Gene-Symbol | GenBank ID |
|---|---|
| ANTXR1 | GI_16933552 |
| ANXA2 | GI_4757755 |
| AP2B1 | GI_4557468 |
| APRIN | GI_7657268 |
| AQP3 | GI_22165421 |
| AR | GI_21322251 |
| ARD1 | GI_34222259 |
| AREG | GI_22035683 |
| ARF6 | GI_6996000 |
| ARFGAP3 | GI_28416437 |
| ARFIP2 | GI_6912601 |
| ARHGEF7 | GI_22027526 |
| ATF2 | GI_22538421 |
| ATP2C1 | GI_7656909 |
| ATP6V1E2 | GI_33669104 |
| AZGP1 | GI_38372939 |
| BART1 | GI_17978472 |
| BAX | GI_34335114 |
| BBC1 | GI_15431296 |
| BBC3 | GI_24475588 |
| BC008967 | GI_24308353 |
| BC-2 | GI_38372936 |
| BCATm | GI_4502374 |
| BCL2A | GI_4557354 |
| BCL2B | GI_4557356 |
| BDH | GI_34304349 |
| BGN | GI_34304351 |
| BHC80 | GI_19923461 |
| BIK | GI_21536418 |
| BMP5 | GI_24797149 |
| BMP7 | GI_4502426 |
| BMPR1B | GI_4502430 |
| BNIP3 | GI_7669480 |
| BTF3 | GI_29126237 |
| BTG2 | GI_28872718 |
| C18orf8 | GI_21361441 |
| C20orf46 | GI_8922926 |
| C6orf56 | GI_7662247 |
| C7 | GI_4557386 |
| CALD1 | GI_15149468 |
| CALM1 | GI_31377794 |
| CAMKK2 | GI_27437014 |
| CANX | GI_31542290 |
| CAPL | GI_9845514 |
| CAPZB | GI_4826658 |
| CAV1 | GI_15451855 |
| CAV2 | GI_38176290 |
| CCK | GI_4755130 |
| CCNE2 | GI_17318566 |
| CD24 | GI_7019342 |
| CD38 | GI_38454325 |
| CD3G | GI_339406 |
| CD44 | GI_21361192 |
| CDC42BPA | GI_30089961 |
| CDC6 | GI_16357469 |
| CDH1 | GI_14589887 |
| CDH11 | GI_16306531 |
| CDKN1B | GI_17978497 |
| CDKN2A | GI_17738299 |
| CDKN2B | GI_17981693 |
| cDNA clone | GI_10437016 |
| cDNA clone | GI_1178507 |
| cDNA clone | GI_1580637 |
| cDNA clone | GI_16550429 |
| cDNA clone | GI_2056367 |
| cDNA clone | GI_22761402 |
| cDNA clone | GI_3043194 |
| cDNA clone | GI_4884218 |
| cDNA clone | GI_6504179 |
| cDNA clone | GI_674501 |
| cDNA clone | GI_6993120 |
| cDNA clone | GI_9120119 |
| cDNA clone | GI_9877016 |
| cDNA clone | GI_1307897 |
| cDNA clone | GI_1963114 |
| cDNA clone | GI_3253738 |
| cDNA clone | GI_1193025 |
| cDNA clone | GI_1628918 |
| cDNA clone | GI_2094528 |
| cDNA clone | GI_2103530 |
| cDNA clone | GI_2805998 |
| cDNA clone | GI_3181305 |
| cDNA clone | GI_3253412 |
| cDNA clone | GI_3596138 |
| cDNA clone | GI_839562 |
| cDNA clone | GI_880122 |
| cDNA clone | GI_2325568 |
| cDNA clone | GI_1309053 |
| cDNA clone | GI_3360414 |
| CDS2 | GI_22035625 |
| CES1 | GI_16905523 |
| CETN2 | GI_4757901 |
| CHAF1A | GI_4885106 |
| CHGA | GI_10800418 |
| CKAP4 | GI_19920316 |
| CKTSF1B1 | GI_37693998 |
| CLDN7 | GI_34222214 |
| CLU | GI_4502904 |
| CLUL1 | GI_34222143 |
| c-maf | GI_3335147 |
| CNN1 | GI_34222150 |
| COBLL1 | GI_7662427 |
| COL1A1 | GI_14719826 |
| COL1A2 | GI_21536289 |
| COL3A1 | GI_15149480 |
| COL4A1 | GI_17017989 |
| COL4A2 | GI_17986276 |
| COL5A2 | GI_16554580 |
| COPE | GI_31542318 |
| COPEB | GI_37655156 |
| CPXM | GI_29171731 |
| CRISP3 | GI_5174674 |
| CRYAB | GI_4503056 |
| CSMD1 | GI_15100167 |
| CSPG2 | GI_21361115 |
| CST3 | GI_19882253 |
| CTBP1 | GI_4557496 |
| CTHRC1 | GI_34147546 |
| CTSH | GI_23110954 |
| CXCL1 | GI_4504152 |
| CYP1B1 | GI_13325059 |
| DAT1 | GI_21361801 |
| DC13 | GI_9910183 |
| DCC | GI_4885174 |
| DCK | GI_4503268 |
| DD3 | GI_6165973 |
| DDR1 | GI_38327631 |
| DEPC-1 | GI_21040274 |
| DF | GI_4503308 |
| DHCR24 | GI_13375617 |
| DHPS | GI_7108341 |
| DIO2 | GI_7549804 |
| DKFZp434C0931 | GI_32880207 |
| DKFZP564B167 | GI_7661601 |
| DKFZp586J0119 | GI_26986531 |
| DKFZp586N1423 | GI_4729049 |
| DKFZp761D221 | GI_14150038 |
| DLG2 | GI_4557526 |
| DLG3 | GI_10863920 |
| DNAH5 | GI_19115953 |
| D-PCa-2 | GI_27734694 |
| D-PCa-2 | GI_30314327 |
| D-PCa-2 | GI_30314331 |
| drn3 | GI_18375529 |
| ECT2 | GI_21735571 |
| EDNRB | GI_4557546 |
| EEF1G | GI_25453475 |
| EEF2 | GI_25453476 |
| EGFR | GI_29725608 |
| EGR1 | GI_31317226 |
| EIF4EL3 | GI_4757701 |
| ELAC2 | GI_34147640 |

TABLE 3-continued 512 genes selected for this study.

| Gene-Symbol | GenBank ID |
|---|---|
| ERBB2 | GI_4758297 |
| ERBB3 | GI_4503596 |
| ERG1 | GI_33667106 |
| ERG2 | GI_7657065 |
| ESM1 | GI_13259505 |
| EXOC7 | GI_24308034 |
| EXT1 | GI_4557570 |
| EZH2 | GI_23510382 |
| F2R | GI_6031164 |
| F5 | GI_10518500 |
| FASN | GI_21618358 |
| FAT | GI_4885228 |
| FBP1 | GI_16579887 |
| FGF18 | GI_4503694 |
| FGF2 | GI_15451897 |
| FGF4 | GI_4503700 |
| FGFR2 | GI_13186258 |
| FGR | GI_4885234 |
| FLJ12443 | GI_33946290 |
| FLJ30473 | GI_21389616 |
| FLT1 | GI_32306519 |
| FOLH1 | GI_4758397 |
| FOS | GI_6552332 |
| FRZB | GI_38455387 |
| FSTL1 | GI_34304366 |
| FZD7 | GI_4503832 |
| G2AN | GI_38371757 |
| G6PD | GI_21614519 |
| GABRG2 | GI_4557610 |
| GAGEC1 | GI_19747284 |
| GALNT1 | GI_13124890 |
| GALNT3 | GI_9945386 |
| GARNL3 | GI_34222344 |
| GAS1 | GI_4503918 |
| GDEP | GI_24475750 |
| GDF15 | GI_4758935 |
| GDI2 | GI_6598322 |
| GJA1 | GI_4755136 |
| GMPS | GI_4504034 |
| GNAZ | GI_4504050 |
| GNE | GI_6382074 |
| GPR126 | GI_37620168 |
| GPR43 | GI_4885332 |
| GRP | GI_34222290 |
| GRPR | GI_4885360 |
| GSPT1 | GI_4504166 |
| GSPT2 | GI_8922423 |
| GSTA1 | GI_22091453 |
| GSTM1 | GI_23065543 |
| GSTM3 | GI_23065551 |
| GSTM4 | GI_23065554 |
| GSTM5 | GI_23065562 |
| GSTP1 | GI_6552334 |
| GUCY1A3 | GI_4504212 |
| hAG-2/R | GI_20070225 |
| HDAC9 | GI_7662279 |
| HGF | GI_33859834 |
| HLA-DPB1 | GI_24797075 |
| HLTF | GI_21071051 |
| HMG20B | GI_5454079 |
| HNF-3 alpha | GI_24497500 |
| HNMP-1 | GI_4503562 |
| HNRPAB | GI_14110401 |
| HOXC6 | GI_24497542 |
| HPN1 | GI_33695154 |
| HPN2 | GI_4504480 |
| hRVP1 | GI_21536298 |
| HSA250839 | GI_8923753 |
| HSD17B4 | GI_4504504 |
| HUEL | GI_7656945 |
| ID2 | GI_33946335 |
| IER3 | GI_16554596 |
| IFI27 | GI_5031780 |
| IGF1 | GI_19923111 |
| IGF2 | GI_6453816 |
| IGFBP2 | GI_10835156 |
| IGFBP3 | GI_19923110 |
| IGFBP5 | GI_46094066 |
| IL1R1 | GI_27894331 |
| ILK | GI_4758605 |
| ILKAP | GI_29171685 |
| IMPDH2 | GI_4504688 |
| INHBA | GI_4504698 |
| ITGA1 | GI_20545279 |
| ITGA5 | GI_4504750 |
| ITGB1 | GI_19743812 |
| ITGB3 | GI_4557676 |
| ITGBL1 | GI_4758613 |
| ITPR1 | GI_10835022 |
| ITPR3 | GI_4504794 |
| ITSN | GI_3859852 |
| JUNB | GI_4504808 |
| KAI1 | GI_13259537 |
| KCNRG | GI_27734696 |
| KHDRBS3 | GI_5730072 |
| KIAA0003 | GI_21328452 |
| KIAA0152 | GI_7661947 |
| KIAA0172 | GI_23510374 |
| KIAA0389 | GI_4826845 |
| KIAA0664 | GI_24308018 |
| KIAA0869 | GI_29789057 |
| KIAA1109 | GI_42656961 |
| KIAA1946 | GI_29126182 |
| KIAK0002 | GI_16950656 |
| KIP | GI_9951921 |
| KIP2 | GI_4557440 |
| KLK2 | GI_20149573 |
| KLK3 | GI_22208990 |
| KLK4 | GI_24234714 |
| KNTC2 | GI_5174456 |
| K-ras | GI_34485723 |
| KRT12 | GI_4557698 |
| KRT13 | GI_24234693 |
| KRT15 | GI_24430189 |
| KRT5 | GI_17318577 |
| KRT8 | GI_4504918 |
| LAMA4 | GI_9845494 |
| LAMB1 | GI_4504950 |
| LAMR1 | GI_9845501 |
| LDHA | GI_5031856 |
| LIM | GI_5453713 |
| LIMK1 | GI_8051616 |
| LIPH | GI_21245105 |
| LMNB1 | GI_27436949 |
| LOC119587 | GI_39930572 |
| LOC129642 | GI_20270350 |
| LOC283431 | GI_28372562 |
| LOC400665 | GI_42661841 |
| LOC92689 | GI_29789372 |
| LOX | GI_21264603 |
| LSAMP | GI_4505024 |
| LTB4DH | GI_34222094 |
| LTBP2 | GI_4557732 |
| LTBP4 | GI_4505036 |
| LU | GI_31543105 |
| LUM | GI_21359858 |
| MADH4 | GI_34147555 |
| MAL | GI_12408666 |
| MAP2K1IP1 | GI_21614526 |
| MAP3K10 | GI_21735549 |
| MCCC2 | GI_14251210 |
| MCM2 | GI_33356546 |
| MCM3 | GI_33356548 |
| MCM4 | GI_33469918 |
| MCM5 | GI_23510447 |
| MCM6 | GI_33469920 |
| MCM7 | GI_33469967 |
| MEIS2 | GI_27502374 |
| MELK | GI_7661973 |
| memD | GI_3183974 |
| MET | GI_4557746 |
| MGC45594 | GI_31342226 |

TABLE 3-continued 512 genes selected for this study.

| Gene-Symbol | GenBank ID |
|---|---|
| MIC-1 | GI_2674084 |
| MKI67 | GI_19923216 |
| MLCK | GI_16950610 |
| MLP | GI_32401423 |
| MME | GI_6042205 |
| MMP1 | GI_13027798 |
| MMP14 | GI_13027797 |
| MMP2 | GI_11342665 |
| MMP7 | GI_13027804 |
| MMP9 | GI_4826835 |
| MNAT1 | GI_4505224 |
| MOAT-B | GI_34452699 |
| MPDZ | GI_4505230 |
| MS4A7 | GI_23110999 |
| MSR1 | GI_20357509 |
| MT3 | GI_5174761 |
| MYBL2 | GI_31652260 |
| MYC | GI_31543215 |
| N2A3 | GI_2967518 |
| NBL1 | GI_33519445 |
| NDUFA2 | GI_32171239 |
| NEFH | GI_32483415 |
| NELL2 | GI_5453765 |
| NETO2 | GI_24041025 |
| NGFB | GI_4505390 |
| NIPA2 | GI_34147393 |
| NKX3-1 | GI_19923351 |
| nm23-H2 | GI_4505408 |
| NME1 | GI_38045911 |
| NMU | GI_5729946 |
| NOS1 | GI_10835172 |
| NOS2A | GI_24041028 |
| NOX4 | GI_20149638 |
| NR4A1 | GI_27894342 |
| NRAS | GI_6006027 |
| NRG1 | GI_4758525 |
| NRIP1 | GI_4505454 |
| NSP | GI_10863934 |
| NTN1 | GI_4758839 |
| NTRK3 | GI_4505474 |
| NUDT3 | GI_37622350 |
| NY-REN-41 | GI_18087816 |
| ODC1 | GI_4505488 |
| OPRS1 | GI_22212932 |
| ORC6L | GI_32454755 |
| OSBPL8 | GI_22035617 |
| OXCT | GI_4557816 |
| P1 | GI_31542946 |
| P4HB | GI_20070124 |
| PAICS | GI_17388802 |
| PART1 | GI_11496986 |
| PCGEM1 | GI_11066459 |
| PCNA | GI_33239449 |
| PDE3B | GI_4505660 |
| PDGFRB | GI_15451788 |
| PDLIM7 | GI_11496884 |
| PECI | GI_5174624 |
| PEX5 | GI_37059745 |
| PGM3 | GI_7661567 |
| PIM1 | GI_31543400 |
| PKCI-1 | GI_29135342 |
| PLA2G2A | GI_20149501 |
| PLA2G7 | GI_23512330 |
| PLS3 | GI_28416938 |
| PMI1 | GI_4505234 |
| PPAP2B | GI_29171739 |
| PPFIA3 | GI_32189361 |
| PPP1CB | GI_4506004 |
| PPP1R12A | GI_4505316 |
| PRC1 | GI_4506038 |
| PRKCL2 | GI_5453973 |
| PRO1489 | GI_7959775 |
| PROK1 | GI_14165281 |
| Prostein | GI_14916436 |
| PRSS8 | GI_21536453 |
| PSCA | GI_29893565 |
| PSM | GI_190663 |
| PSK | GI_7706400 |
| PTEN | GI_4506248 |
| PTGDR | GI_28466968 |
| PTGDS | GI_32171248 |
| PTGS2 | GI_4506264 |
| PTK9 | GI_31543447 |
| PTOV1 | GI_33695089 |
| PTTG1 | GI_11038651 |
| PYCR1 | GI_24797096 |
| RAB2 | GI_4506364 |
| RAB3B | GI_19923749 |
| RAB5A | GI_31543538 |
| RAB6B | GI_7706674 |
| RAMP | GI_7705575 |
| RAN | GI_6042206 |
| RANGAP1 | GI_38201688 |
| rapt1GAP | GI_4506414 |
| RB1 | GI_4506434 |
| RBM5 | GI_5032030 |
| RBP1 | GI_8400726 |
| REPS2 | GI_4758943 |
| RET | GI_21536316 |
| RFC4 | GI_31881681 |
| RGS10 | GI_11184225 |
| RGS11 | GI_4506506 |
| RGS5 | GI_4506518 |
| RIG | GI_5454007 |
| RNASEL | GI_30795246 |
| ROBO1 | GI_19743804 |
| RPL13A | GI_14591905 |
| RPL18A | GI_15431299 |
| RPLP0 | GI_16933547 |
| RPS2 | GI_15055538 |
| RRAS | GI_20127497 |
| RRN3 | GI_21361630 |
| SALL4 | GI_37595567 |
| SCUBE2 | GI_10190747 |
| SEC14L2 | GI_7110714 |
| SELENBP1 | GI_16306549 |
| SEPP1 | GI_4885590 |
| SERPINB5 | GI_4505788 |
| SERPINF1 | GI_34098937 |
| SFN | GI_30102938 |
| SGK | GI_25168262 |
| SIAT1 | GI_27765094 |
| SIAT7D | GI_28373089 |
| SIM2 | GI_7108363 |
| SLC14A1 | GI_7706676 |
| SLC25A6 | GI_27764862 |
| SLC2A3 | GI_5902089 |
| SLC39A6 | GI_12751474 |
| SLC43A1 | GI_34222288 |
| SLIT3 | GI_11321570 |
| SND1 | GI_7657430 |
| SOCS2 | GI_21536304 |
| SOLH | GI_5032104 |
| SPARC | GI_4507170 |
| SPARCL1 | GI_21359870 |
| SPDEF | GI_6912579 |
| SPOCK | GI_15451924 |
| SQRDL | GI_10864010 |
| SRD5A2 | GI_14557854 |
| Stac | GI_4507246 |
| STEAP | GI_22027487 |
| STEAP2 | GI_25092600 |
| STK39 | GI_7019542 |
| STOM | GI_38016910 |
| STRA13 | GI_21450710 |
| SULF1 | GI_29789063 |
| SYNE1 | GI_41281986 |
| SYT7 | GI_38194226 |
| TACSTD1 | GI_4505058 |
| TBXA2R | GI_27545324 |
| TCF2 | GI_6031204 |
| TFAP2C | GI_19923162 |

TABLE 3-continued

512 genes selected for this study.

| Gene-Symbol | GenBank ID |
| --- | --- |
| TFCP2 | GI_34147661 |
| TGFA | GI_4507460 |
| TGFB1 | GI_10863872 |
| TGFB2 | GI_4507462 |
| TGFB3 | GI_4507464 |
| TGFBR3 | GI_4507470 |
| TGM4 | GI_4507478 |
| THBD | GI_4507482 |
| THBS1 | GI_4507484 |
| TIMP1 | GI_4507508 |
| TIMP2 | GI_9257247 |
| TMEPAI | GI_21361840 |
| TMSNB | GI_11496272 |
| TNFRSF6 | GI_23510419 |
| TNFSF10 | GI_23510439 |
| tom1-like | GI_4885638 |
| TP53 | GI_8400737 |
| TP73 | GI_4885644 |
| TP73L | GI_31543817 |
| TRAF2 | GI_22027611 |
| TRAF4 | GI_22027621 |
| TRAF5 | GI_22027625 |
| TRAP1 | GI_7706484 |
| TRIM29 | GI_17402908 |
| TROAP | GI_33438581 |
| TRPM8 | GI_21361690 |
| TSPAN-1 | GI_21264577 |
| TSPYL5 | GI_29789280 |
| TU3A | GI_6005923 |
| TUSC3 | GI_30410787 |
| TYMS | GI_4507750 |
| UAP1 | GI_34147515 |
| UB1 | GI_30089964 |
| UBE2C | GI_32967292 |
| UBE2L6 | GI_38157980 |
| UBE2S | GI_7657045 |
| UCHL5 | GI_7706752 |
| UNC5C | GI_16933524 |
| VCL | GI_7669551 |
| WISP1 | GI_18490998 |
| Wnt5A | GI_17402917 |
| XBP1 | GI_14110394 |
| XLKD1 | GI_5729910 |
| ZABC1 | GI_5730123 |
| ZAKI-4 | GI_5032234 |
| ZFP36 | GI_4507960 |

Example II

Gene Expression Profiles Predict Relapse of Prostate Cancer

This example shows the correlation between GEX score for a collection of 16 genes and prostate cancer relapse.

Figure 2:
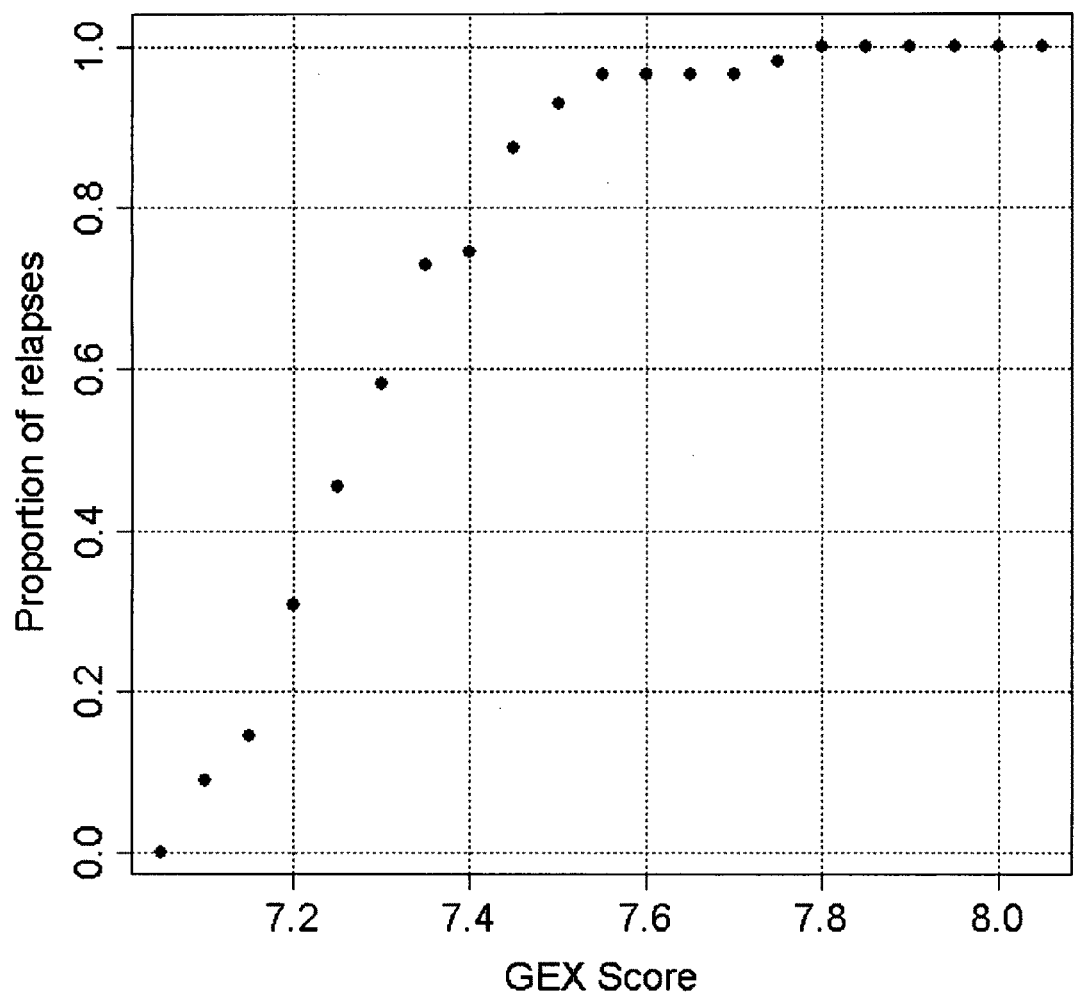
FIG. 2 shows a plot of percentage of relapse cases vs. the GEX score.

As shown in FIG. 2, there was a good correlation between the GEX score and relapse and a near-linear increase in percent of relapse cases with GEX score between 7 and 7.6 (FIG. 2). For instance, when GEX score was 7.4, approximately 75% of the cases relapsed. When the GEX score reached 7.8, 100% of the cases relapsed. It is worth noting that the average GEX score was 7.2 for GS7 patients without relapse and 7.4 for GS7 patients who relapsed, corresponding to 20% and 75% of the chance of relapse, respectively.

Figure 3:
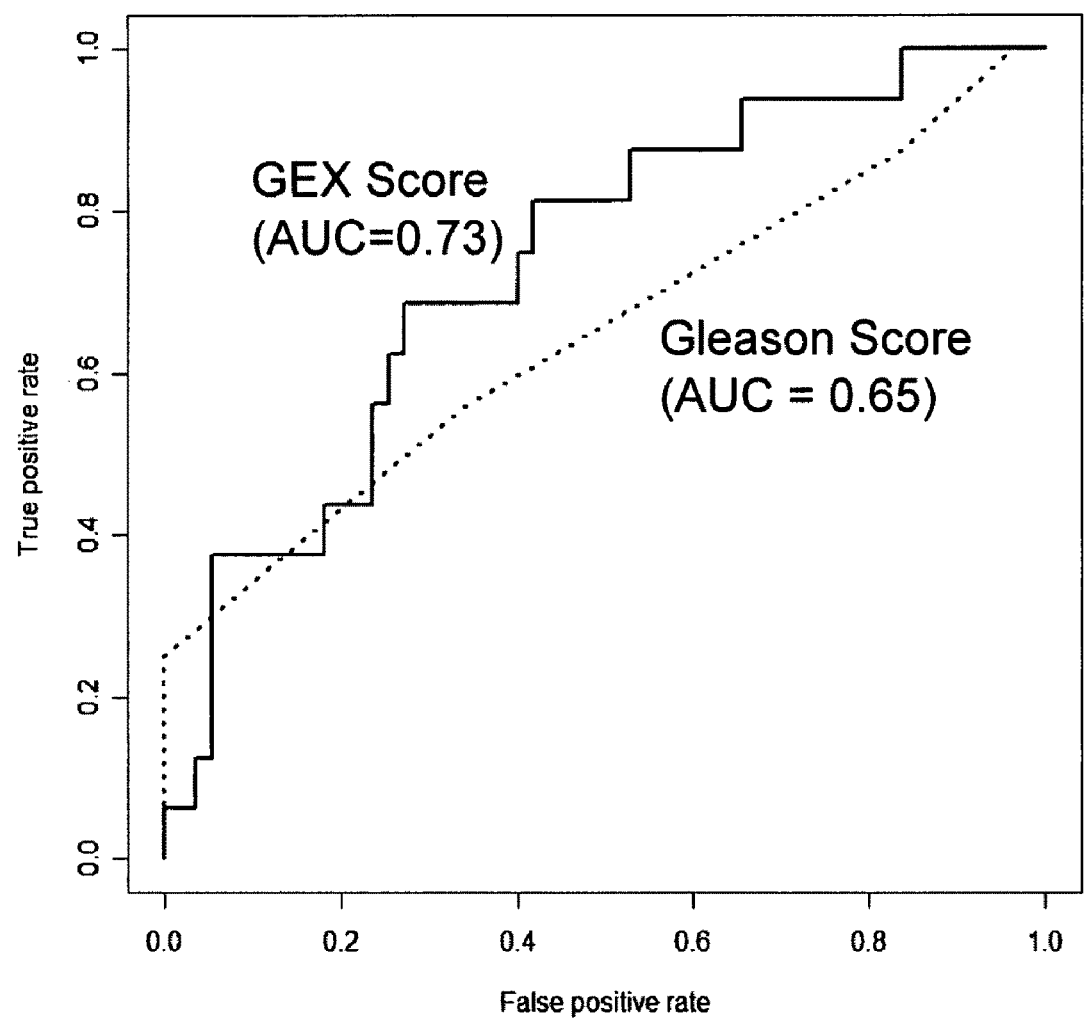
FIG. 3 shows a Receiver Operating Characteristic (ROC) curve for relapse prediction in prostate cancer. False positive is defined as a case with no relapse, but high score. The connected line shows the performance of GEX and the dotted line shows the performance of Gleason score.

The Receiver Operating Characteristic (ROC) curve showed that the 16 gene expression signature was more predictive of relapse than Gleason score (FIG. 3). The GEX score had an AUC (Area Under the Curve) of 0.73, which was better than Gleason score with an AUC 0.65. The Sensitivity and Specificity of relapse prediction were 0.69 and 0.69 for GEX score>7.337 (corresponding to mean GEX score of all samples with Gleason scores 7 and 8), and 0.56 and 0.65 for Gleason score>7. Particularly, the GEX score improved the relapse prediction in patients with a Gleason score 7 (see FIG. 1), benefiting from the continuous analogy of Gleason score.

Figure 4:
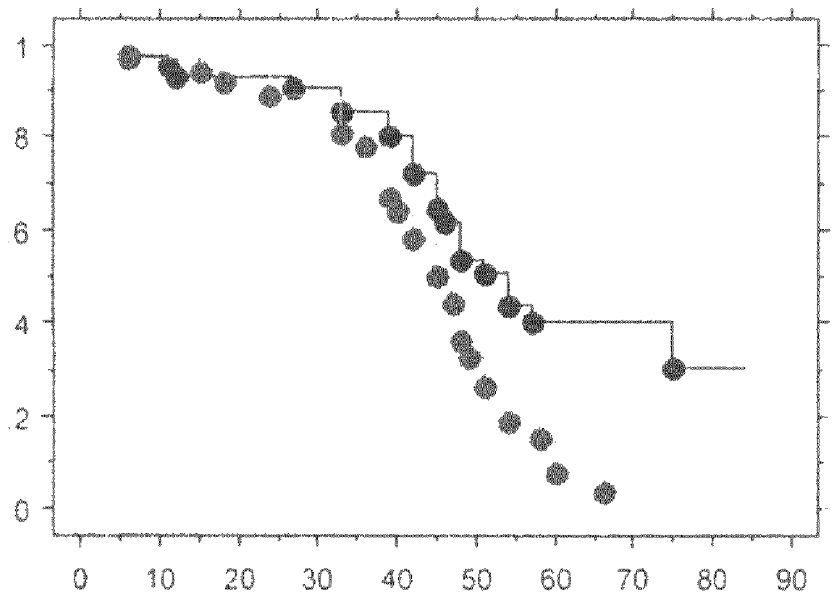
FIG. 4 shows Kaplan-Maier analysis of relapse (N=71). X-axis: Time to relapse (days); Y-axis: Relapse free probability. (A) Relapse prediction based on expression signature, GEX>7.337, p=0.0044; (B) Relapse prediction based on Gleason score, Gleason score>7 (p=0.138)

Patients that experienced relapse tended to have higher GEX scores despite having identical Gleason scores. The most pronounced difference was observed in GS7 patients (two-sided t-test p=0.005, when GS7-Y compared to GS7-N, FIG. 1). The GEX scores, when divided among the groups of GEX>7.3 and <=7.3 (cutoff was chosen as median GEX for GS7 and GS8 samples), had a significant correlation with subsequent relapse in the Kaplan-Meier analysis (FIG. 4, p=0.007). Among the GS7 patients, 1/21 of GS3+4 and 4/11 of GS4+3 relapsed respectively (Fisher Exact test p=0.037). The mean GEX scores were 7.236 and 7.305 for the two groups, respectively (p=0.071 for hypothesis testing increased GEX score for 4+3 patients). GS alone was associated with relapse versus no relapse (p=0.02). Neither the tumor stage nor the risk groups assigned at the time of biopsy significantly correlated with relapse (Kaplan-Meier analysis, p=0.07 and 0.1, respectively).

Only samples (N=71: 55 without relapse and 16 with relapse) with no residual tumor after surgery were considered (with the exception of three cases, which had non-detectable serum PSA after surgery, but had positive margins) and patients which received therapy and had no relapse were excluded, the lack of relapse could not be due to selective therapies but has to be due to the underlying biological difference among these patients.

GEX scores of the 34 matched, non-tumor prostate tissues also generated a mean of 7.19±0.18, lower than that in the tumor samples (7.25±0.25), and the GEX on non-tumor tissues appeared to correlate with relapse on Kaplan-Meier analysis (p=0.04), although not as significant as the tumor itself.

Four cases of FFPE prostate cancer tissue sections were de-paraffinized in xylene and re-hydrated in ethanol. Antigen retrieval was performed by steam heating with 1× DAKO Target Retrieval solution. The sections were then allowed to cool to room temperature in the solution. The endogenous peroxidase was removed by 3% $H_2O_2$. Non-specific binding of biotin and avidin was blocked by blocking solution for 30 minutes (Protein Block Serum-Free, DAKO, Carpinteria, Calif.). The background staining was reduced with incubation of goat serum (1:20 dilution) for 60 minutes. Primary antibodies (HOXC6 1:100, Aviva Systems Biology, and Ki-67 1:200, DAKO) were placed on slides and incubated for 1 hour at room temperature in the case of Ki-67 and overnight at room temperature in the case of HOXC6. Secondary antibodies conjugated with Streptavidin/HRP (LSAB2, DAKO) were used. The slides were washed and antibody complex visualized by 3,3'-diaminobenzidine (DAB, DAKO). The nuclei were counterstained by Gill's II Hamatoxylin. Immunoactivity in the tissues was estimated by counting the number of positive cells per 1,000 tumor cells. Cases were considered positive if more than 20% of the tumor cells were staining.

Figure 5:
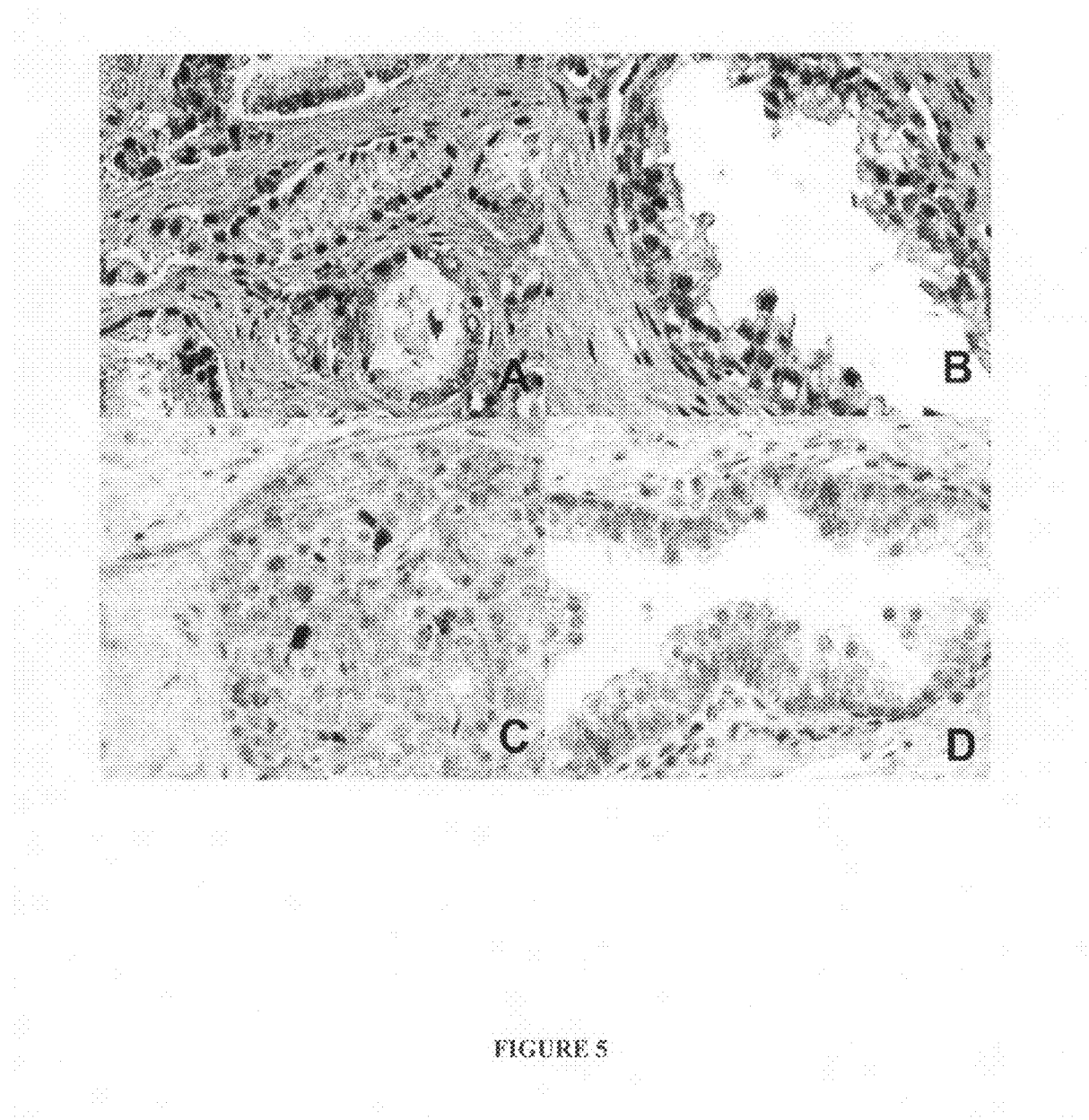
FIG. 5 shows immunohistochemical stains of HOXC6 and Ki67 in tumor cells. Immunohistochemical stains for HOXC6 showed strong nuclear stains in the prostate cancer cells (A) whereas the normal adjacent glands (B) did not show any staining. Ki67 showed variable nuclear stains in the tumor cells (C), but much less stain in the nearby normal prostate glands (D). All magnifications are 400×.

As shown in FIG. 5, immunohistochemistry of HOXC6 showed distinct stain on the tumor nuclei. Compared to adjacent benign prostatic glands, the stain appeared to be restricted to tumor glands, although some benign glands also seemed to have weak signals. The findings supported the gene expression results described above. Ki67 also showed nuclear stain in the tumor cells; however, quantitatively varied between glands.

The gene expression score (GEX) derived from the expression levels of the 16 genes was used to predict relapse of prostate cancer. It is worth pointing out that there was no "training/fitting" made toward their prognostic power at the gene selection step. Making continuous analogy of Gleason grade increased molecular resolution, especially at GS=7-8, in which patients can be stratified better based on their gene expression profiles (FIG. 1); in turn, this translates to a good predictor of relapse for prostate cancer (FIG. 4).

Figure 1:
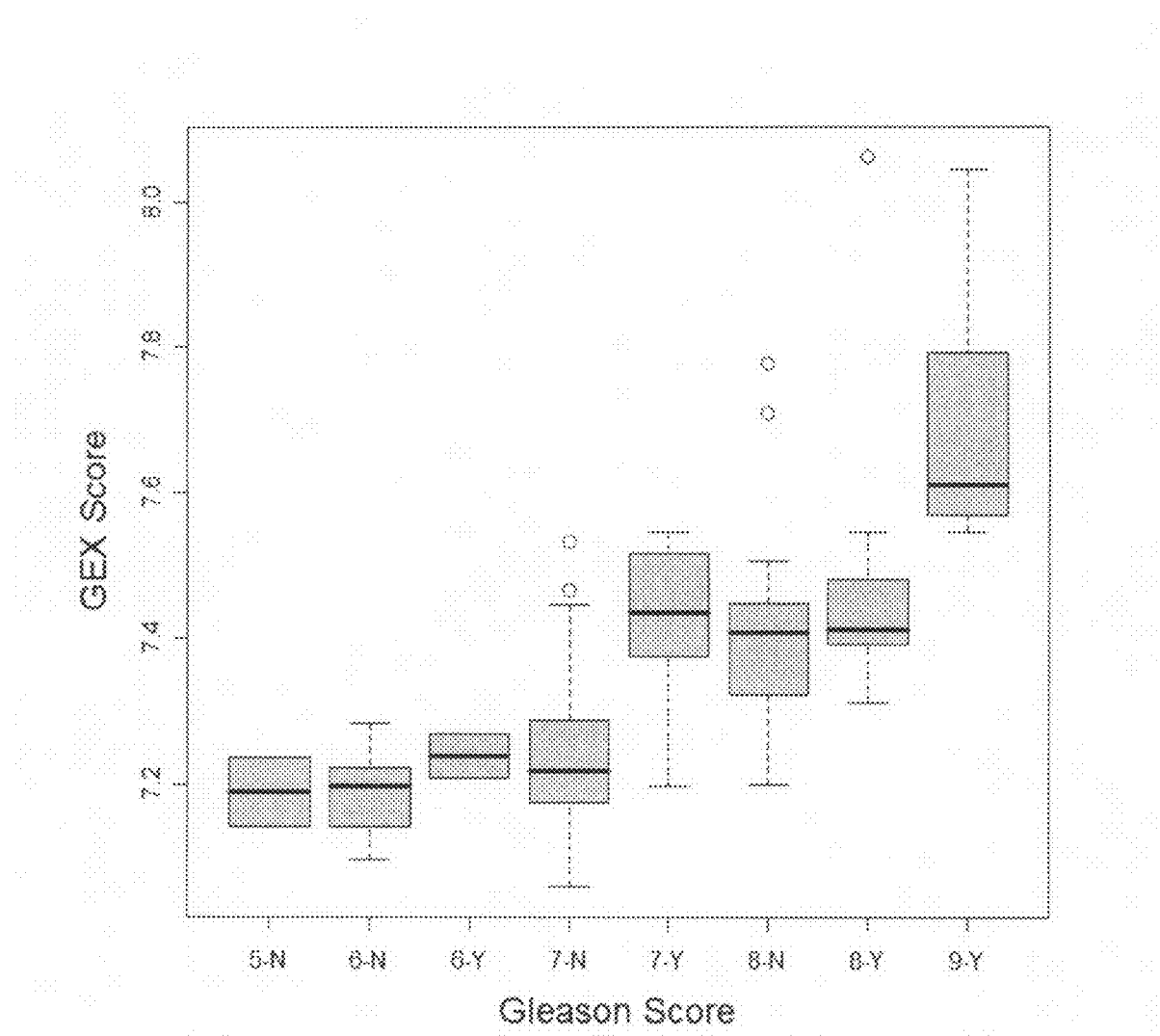
FIG. 1 shows the correlation between gene expression signature and Gleason score. 5-N, 6-N, 7-N and 8-N, correspond respectively to patient groups with Gleason score of 5, 6, 7 and 8 without relapse. 6-Y, 7-Y, 8-Y and 9-Y, correspond respectively to patient groups with Gleason score of 6, 7, 8 and 9 with relapse.

Interestingly, the GEX score exhibited a nonlinear pattern, in which the expression signature score stayed flat when GS<7, and started rising at GS=7 and plateaued at GS=9 (FIG. 1). This suggests that there may be three distinct molecular stages among the prostate cancer patients, and this may have corresponded to Gleason scores 6, 7, and 8, respectively. GEX profiles can potentially identify a subset of histologically intermediate-grade tumors that have more aggressive clinical behavior, i.e. to separate out GS7 patients who were more likely to relapse.

GEX scores were also calculated in the "matched" non-tumor prostate tissues in the same population. The GEX scores were lower than those seen in the tumor glands but the scores had statistically significant correlation with disease relapse (p=0.04). However, the statistical significance was much less than the GEX in the tumor glands (p=0.007). It is possible that the most robust signals generated by GEX came from the tumor glands. However, it is highly plausible that the stromal signals also contributed to the overall GEX score. Additional clinical trials can be performed to test whether non-tumor stroma generate signals that can predict relapse. For example small samples, such as those obtained using LCM in needle biopsies, with or without tumor glands, can be used to assess prognostic outcomes prior to definitive therapy.

The sensitivity and specificity of the 16 gene markers can be validated in another independent cohort and prospectively in clinical trials where patients undergo prostate needle biopsy for diagnosis of carcinoma. This test can give information on diagnosis as well as prognosis through needle biopsy samples. Such a test provides, a mature diagnostic test that is technically simple and applicable for routine clinical use, and can eventually be incorporated into existing prostate cancer nomograms In sum, the above examples show identification of signature genes and subsequent compilation of a set of signature genes capable of establishing a molecular signature that can be used to predict relapse in individuals treated for prostate cancer. The molecular signature described herein replicates across independent sample sets and represents a better expression signature with higher specificity and sensitivity than previously available. As described herein, the principles underlying these examples can be applied to other cancer types as well as other conditions.

Example III

An Expanded Collection of Signature Genes that Predict Relapse of Prostate Cancer This example shows the correlation between GEX score for a collection of 21 genes and prostate cancer relapse.

The correlation between GEX score and Gleason score was re-evaluated for the set of 512 genes shown in Table 3 as follows. GEX score was determined for each of the 512 genes in each of the 71 samples as described in Example I. All genes that had a correlation outside of the median ±2 standard deviations were identified. This resulted in the addition of the GI_2094528, KIP2, NRG1, NBL1, and Prostein genes to the list of 16 genes described in Examples I and II. The resulting collection of 21 genes shown in Table 4.

TABLE 4

Collection of 21 signature genes

| GeneID | Correlation |
| --- | --- |
| CCNE2 | 0.36426 |
| CDC6 | 0.37274 |
| FBP1 | 0.33746 |
| HOXC6 | 0.50382 |
| MKI67 | 0.39223 |
| MYBL2 | 0.37886 |
| PTTG1 | 0.38212 |
| RAMP | 0.44857 |
| UBE2C | 0.32517 |
| Wnt5A | 0.39458 |
| memD | 0.35123 |
| GI_2094528 | 0.30986 |
| KIP2 | −0.31881 |
| NRG1 | −0.27405 |
| NBL1 | −0.32061 |
| Prostein | −0.26023 |
| AZGP1 | −0.35498 |
| CCK | −0.34259 |
| MLCK | −0.34564 |
| PPAP2B | −0.35176 |
| PROK1 | −0.36189 |

The list of 21 genes in Table 4 was evaluated to rank the genes according to the probability that each individual gene was included in a set of genes that was correlated with Gleason score. The ranked list of 21 genes is shown in Table 5. The rank was determined as follows. All combinations of the 21 genes were placed in a Boolean matrix having 21 columns (1 for each gene) and 2,097,151 lines (number of combinations of 1 to 21 into 21). The GEX scores were calculated for each combination using this matrix and the results of the fitted linear models (using rlm function as described in Example I). A Kaplan-Meier analysis was run for each combination and the resulting p-values were stored. The distribution of p-values was plotted for each of the 21 genes and the $3^{rd}$ quartile p-value was determined for each gene. The gene with the highest $3^{rd}$ quartile p-value was removed (i.e. Prostein which had a $3^{rd}$ quartile p-value of 0.053866667 as shown in Table 5). The process was repeated for a Boolean matrix of the 20 remaining genes (i.e. all genes in Table 5 except Prostein). In the second repetition NBL1 was identified and the process repeated again for a matrix of 19 genes including those listed in Table 5 with the exception of Prostein and NBL1. The process was repeated until all genes had been ranked such that the first gene to be removed was ranked last and the final remaining gene was ranked first.

TABLE 5

Ranking of 21 genes

| Rank | Gene | $1^{st}$ quartile p-value | median p-value | $3^{rd}$ quartile p-value |
| --- | --- | --- | --- | --- |
| 1 | MKI67 | 0.005149 | 0.005149 | 0.005149 |
| 2 | GI_2094528 | 0.000725185 | 0.001363455 | 0.0020022 |
| 3 | HOXC6 | 0.000229413 | 0.0009615 | 0.002487667 |
| 4 | CCK | 0.000301025 | 0.000641625 | 0.00263825 |
| 5 | memD | 9.14E−05 | 0.00033542 | 0.00104746 |

TABLE 5-continued

Ranking of 21 genes

| Rank | Gene | 1st quartile p-value | median p-value | 3rd quartile p-value |
|---|---|---|---|---|
| 6 | FBP1 | 9.19E–05 | 0.000396633 | 0.001919933 |
| 7 | CDC6 | 5.16E–05 | 0.000166507 | 0.0008572 |
| 8 | PROK1 | 5.60E–05 | 0.000189093 | 0.00107155 |
| 9 | MYBL2 | 6.40E–05 | 0.000227222 | 0.001027144 |
| 10 | UBE2C | 6.93E–05 | 0.00026413 | 0.00109623 |
| 11 | PTTG1 | 0.000119859 | 0.000440473 | 0.001409827 |
| 12 | KIP2 | 0.000137185 | 0.000467458 | 0.001629417 |
| 13 | NRG1 | 0.000170895 | 0.000594477 | 0.002144154 |
| 14 | AZGP1 | 0.000262736 | 0.000879486 | 0.0029995 |
| 15 | MLCK | 0.000320207 | 0.00114972 | 0.004122933 |
| 16 | Wnt5A | 0.000291781 | 0.001149381 | 0.004899125 |
| 17 | PPAP2B | 0.000332412 | 0.001535388 | 0.007228882 |
| 18 | CCNE2 | 0.000598356 | 0.002471444 | 0.0099375 |
| 19 | RAMP | 0.001336737 | 0.005029421 | 0.017818263 |
| 20 | NBL1 | 0.002041885 | 0.0080705 | 0.030194 |
| 21 | Prostein | 0.003319571 | 0.01380119 | 0.053866667 |

As shown in Table 5 the lowest p-values occur for a combination of 7 genes including MKI67, GI_2094528, HOXC6, CCK, memD, FBP1, and CDC6. Thus, the gene expression pattern for this combination of genes provides a particularly useful GEX score for predicting relapse in prostate cancer patients. FIG. 9 shows box plots for the distribution of survival p-values determined from GEX scores for the individual genes and for various combinations from two to seven of the genes. The plots indicate that the GEX score determined from each individual gene is a better predictor of prostate cancer relapse than Gleason score for all but one gene (i.e. CDC6 had a p-value near 0.152 compared to a p-value of 0.138 for Gleason score). Thus, the GEX scores derived individually from MKI67, GI_2094528, HOXC6, CCK, memD, or FBP1 provide a better predictor of prostate cancer relapse than Gleason score. Furthermore, all combinations of two or more of the 7 genes provided a better predictor of prostate cancer relapse than Gleason score. This was the case whether or not CDC6 was a member of the combination. Accordingly, the GEX score for CDC6 is reasonably predictive of prostate cancer relapse.

FIG. 10 shows the Kaplan-Meier plot for a combination of 7 genes including MKI67, GI_2094528, HOXC6, CCK, memD, FBP1, and CDC6. A p-value of $6.45 \times 10^{-5}$ was found for the GEX score determined for the 7 genes. The plot compares very well to the Kaplan-Meier plot for 16 genes (see FIG. 4).

The results above demonstrate that a collection of 21 genes is useful for determining a GEX score that is predictive of prostate cancer relapse. The results also demonstrate methods for identifying sub-combinations of the 21 genes that are predictive of prostate cancer relapse.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

We claim:

1. A method for predicting the probability of relapse of prostate cancer in an individual, said method comprising the steps of
    (a) providing a prostate tissue sample for a test individual;
    (b) providing expression levels for a collection of signature genes from a test individual, wherein said collection of signature genes comprises at least GI_2094528 and MKI67;
    (c) deriving a score that captures said expression levels for said collection of signature genes;
    (d) providing a reference model comprising information correlating said score with prostate cancer relapse; and
    (e) comparing said score to said reference model, thereby determining the probability of prostate cancer relapse for said individual.

2. The method of claim 1, wherein said individual has a Gleason score between seven and eight.

3. The method of claim 2, wherein said Gleason score is based on a primary grade of four.

4. The method of claim 2, wherein said Gleason score is based on a primary grade of three.

5. The method of claim 1, further comprising providing a report having a prediction of prostate cancer relapse for said individual.

6. The method of claim 1, wherein said collection of signature genes comprises GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B, and PROK1.

7. The method of claim 1, wherein said collection of signature genes consists essentially of GI_2094528, KIP2, NRG1, NBL1, Prostein, CCNE2, CDC6, FBP1, HOXC6, MKI67, MYBL2, PTTG1, RAMP, UBE2C, Wnt5A, MEMD, AZGP1, CCK, MLCK, PPAP2B, and PROK1.

8. The method of claim 1, wherein said collection of signature genes further comprises at least one gene selected from the group consisting of CCNE2, CDC6, FBP1, HOXC6, MYBL2, PTTG1, RAMP, UBE2C, Wnt5A, MEMD, AZGP1, CCK, MLCK, PPAP2B, and PROK1.

9. The method of claim 1, wherein said collection of signature genes further comprises at least two genes selected from the group consisting of CCNE2, CDC6, FBP1, HOXC6, MYBL2, PTTG1, RAMP, UBE2C, Wnt5A, MEMD, AZGP1, CCK, MLCK, PPAP2B, and PROK1.

10. The method of claim 1, wherein said collection of signature genes further comprises at least two genes selected from the group consisting of HOXC6, CCK, MEMD, FBP1, and CDC6.

11. The method of claim 1, wherein said collection of signature genes comprises MKI67, GI_2094528, HOXC6, CCK, MEMD, FBP1, and CDC6.

12. The method of claim 1, wherein said collection of signature genes consists essentially of MKI67, GI_2094528, HOXC6, CCK, MEMD, FBP1, and CDC6.

13. The method of claim 1, wherein said score is a better predictor of prostate cancer relapse than Gleason score.

14. The method of claim 1, wherein said collection of signature genes further comprises HOXC6.

15. The method of claim 1, wherein said collection of signature genes further comprises CCK.

16. The method of claim 1, wherein said collection of signature genes further comprises HOXC6 and CCK.

17. The method of claim 1, wherein said collection of signature genes further comprises HOXC6 and MEMD.

18. The method of claim 1, wherein said collection of signature genes further comprises CCK and MEMD.

19. The method of claim 1, wherein said collection of signature genes further comprises FBP1.

20. The method of claim 1, wherein said collection of signature genes further comprises MEMD.

21. The method of claim 1, wherein said collection of signature genes further comprises CDC6.

22. The method of claim 1, wherein said collection of signature genes further comprises at least one gene selected from the group consisting of KIP2, NRG1, NBL1, Prostein, CCNE2, MYBL2, PTTG1, RAMP, UBE2C, Wnt5A, AZGP1, MLCK, PPAP2B, and PROK1.

* * * * *